US010556940B2

(12) United States Patent
Tran et al.

(10) Patent No.: US 10,556,940 B2
(45) Date of Patent: Feb. 11, 2020

(54) T CELL RECEPTORS RECOGNIZING HLA-CW8 RESTRICTED MUTATED KRAS

(71) Applicant: The United States of America, as represented by the Secretary, Department of Health and Human Services, Bethesda, MD (US)

(72) Inventors: Eric Tran, Portland, OR (US); Yong-Chen Lu, Rockville, MD (US); Steven A. Rosenberg, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 133 days.

(21) Appl. No.: 15/758,954

(22) PCT Filed: Sep. 9, 2016

(86) PCT No.: PCT/US2016/050875
§ 371 (c)(1),
(2) Date: Mar. 9, 2018

(87) PCT Pub. No.: WO2017/048593
PCT Pub. Date: Mar. 23, 2017

(65) Prior Publication Data
US 2019/0040111 A1 Feb. 7, 2019

Related U.S. Application Data

(60) Provisional application No. 62/218,688, filed on Sep. 15, 2015.

(51) Int. Cl.
*C07K 14/725* (2006.01)
*G01N 33/574* (2006.01)
*A61K 38/00* (2006.01)

(52) U.S. Cl.
CPC ..... *C07K 14/7051* (2013.01); *G01N 33/5748* (2013.01); *A61K 38/00* (2013.01); *G01N 2333/82* (2013.01)

(58) Field of Classification Search
None
See application file for complete search history.

(56) References Cited

U.S. PATENT DOCUMENTS

| | | | |
|---|---|---|---|
| 8,034,334 | B2 | 10/2011 | Dudley et al. |
| 8,383,099 | B2 | 2/2013 | Dudley et al. |
| 2012/0244133 | A1 | 9/2012 | Rosenberg et al. |

FOREIGN PATENT DOCUMENTS

| | | | |
|---|---|---|---|
| WO | WO 2016/085904 | A1 | 6/2016 |

OTHER PUBLICATIONS

Bonehill et al., "Messenger RNA-electroporated dendritic cells presenting MAGE-A3 simultaneously in HLA class I and class II molecules," *J. Immunol.*, 172(11): 6649-6657 (2004).
Bristol et al., "Identification of a ras oncogene peptide that contains both CD4(+) and CD8(+) T cell epitopes in a nested configuration and elicits both T cell subset responses by peptide or DNA immunization," *Cellular Immunol.*, 205(2): 73-83 (2000).
Cohen et al., "Enhanced antitumor activity of T cells engineered to express T-cell receptors with a second disulfide bond," *Cancer Res.*, 67(8): 3898-903 (2007).
Dudley et al., "Generation of tumor-infiltrating lymphocyte cultures for use in adoptive transfer therapy for melanoma patients," *J. Immunother.*, 26(4): 332-42 (2003).
Gjertsen et al, "HLA-A3 restricted mutant ras specific cytotoxic T-lymphocytes induced by vaccination with T-helper epitopes," *J. Mol. Med.*, 81(1): 43-50 (2003).
Gros et al., "PD-1 identifies the patient-specific $CD8^+$ tumor-reactive repertoire infiltrating human tumors," *J. Clin. Invest.*, 124(5): 2246-2259 (2014).
Haga-Friedman et al., "Incorporation of transmembrane hydrophobic mutations in the TCR enhance its surface expression and T cell functional avidity," *J. Immunol.*, 188(11): 5538-5546 (2012).
International Bureau, International Search Report and Written Opinion in International Application No. PCT/US2016/050875, dated Nov. 11, 2016.
Jin et al., "Simplified method of the growth of human tumor infiltrating lymphocytes in gas-permeable flasks to numbers needed for patient treatment," *J. Immunother.*, 35(3): 283-292 (2012).
Jones et al., "Frequent mutations of chromatin remodeling gene ARID1A in ovarian clear cell carcinoma," *Science*, 330(6001): 228-231 (2010).
Kubuschok et al., "Naturally occurring T-cell response against mutated p21 ras oncoprotein in pancreatic cancer," *Clin. Cancer Res.*, 12(4): 1365-1372 (2006).
Lu et al., "Efficient identification of mutated cancer antigens recognized by T cells associated with durable tumor regressions," *Clin. Cancer Res.*, 20(13): 3401-3410 (2014).
Qin et al., "CD4+ T-cell immunity to mutated ras protein in pancreatic and colon cancer patients," *Cancer Res.*, 55(14): 2984-87 (1995).
Riddell et al., "The use of anti-CD3 and anti-CD28 monoclonal antibodies to clone and expand human antigen-specific T cells," *J. Immunol. Methods*, 128(2): 189-201 (1990).
Rosenberg, "T cells as a Drug for the Personalized Immunotherapy of Cancer," *The Inaugural International Cancer Immunother. Conf.*, Sep. 16, 2015.
Rosenberg et al., "Adoptive cell transfer as personalized immunotherapy for human cancer," *Science*, 348(6230): 62-68 (2015).

(Continued)

*Primary Examiner* — Zachary S Skelding
(74) *Attorney, Agent, or Firm* — Leydig, Voit & Mayer

(57) ABSTRACT

Disclosed is an isolated or purified T cell receptor (TCR) having antigenic specificity for mutated Kirsten rat sarcoma viral oncogene homolog (KRAS) presented in the context of an HLA-Cw*0802 molecule. Related polypeptides and proteins, as well as related nucleic acids, recombinant expression vectors, host cells, populations of cells, and pharmaceutical compositions are also provided. Also disclosed are methods of detecting the presence of cancer in a mammal and methods of treating or preventing cancer in a mammal.

20 Claims, 1 Drawing Sheet

Specification includes a Sequence Listing.

(56) References Cited

OTHER PUBLICATIONS

Shono et al., “Specific T-cell immunity against Ki-ras peptides in patients with pancreatic and colorectal cancers,” *Br. J. Cancer*, 88(4): 530-536 (2003).

Tran et al., “Cancer immunotherapy based on mutation-specific CD4+ T cells in a patient with epithelial cancer,” *Science*, 344(6184): 641-645 (2014).

Tran et al., “Immunogenicity of somatic mutations in human gastrointestinal cancers” and Supplementary Materials, *Science*, 350(6266): 1387-1390 (2015).

Tran, “Cell transfer therapy against somatic mutations in human gastrointestinal cancers,” presentation given at $8^{th}$ Annual Canadian Cancer Immunotherapy Consortium (CICC) Meeting in Vancouver, BC on May 21, 2015.

Tran, “Immunogenicity and immunotherapeutic targeting of somatic mutations inhuman gastrointestinal cancers,” presentation given at $15^{th}$ Annual CCR Fellows and Young Investigators Colloquium at the NCI in Shady Grove, MD on Mar. 23, 2015.

Tran, “Immunogenicity and immunotherapeutic targeting of somatic mutations in human gastrointestinal cancers,” presentation given during a visit to Ottawa Hospital Research Institute, Ottawa, ON, on Jul. 10, 2015.

Tsai et al., “K-Ras4A splice variant is widely expressed in cancer and uses a hybrid membrane-targeting motif,” *PNAS*, 112(3): 779-784 (2015).

Wang et al., “Identification of T-cell Receptors Targeting KRAS-Mutated Human Tumors,” *Cancer Immunol. Res.*, 4(3): 204-214 (2016).

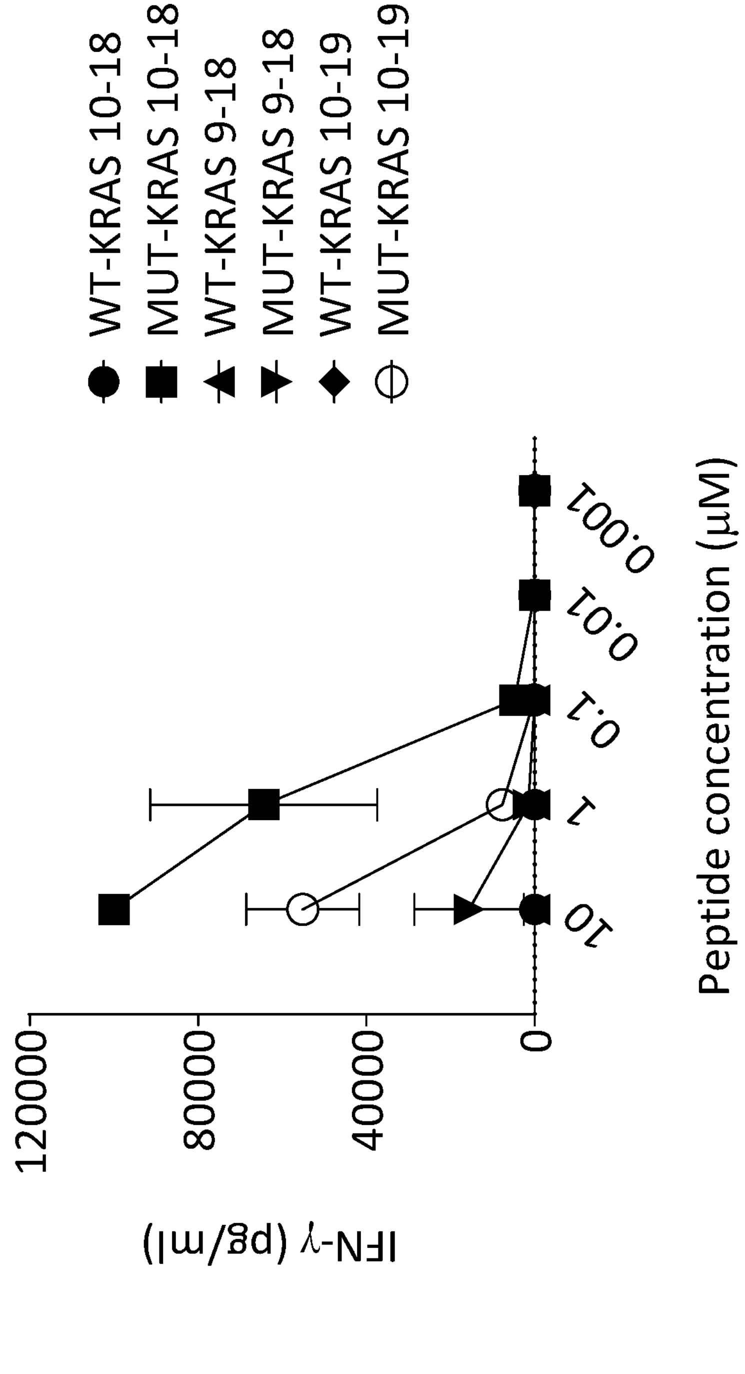
WT-KRAS 10-18
MUT-KRAS 10-18
WT-KRAS 9-18
MUT-KRAS 9-18
WT-KRAS 10-19
MUT-KRAS 10-19
IFN-γ (pg/ml)
120000
80000
40000
0
10
1
0.1
0.01
0.001
Peptide concentration (μM)

T CELL RECEPTORS RECOGNIZING HLA-CW8 RESTRICTED MUTATED KRAS

CROSS-REFERENCE TO RELATED APPLICATIONS

This patent application is the U.S. national stage of International Patent Application Number PCT/US2016/050875, filed Sep. 9, 2016, which claims the benefit of U.S. Provisional Patent Application No. 62/218,688, filed Sep. 15, 2015, each of which is incorporated by reference in its entirety herein.

STATEMENT REGARDING FEDERALLY SPONSORED RESEARCH AND DEVELOPMENT

This invention was made with Government support under project number ZIABC010984 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 30,800 Byte ASCII (Text) file named "737876_ST25.txt," dated Feb. 12, 2018.

BACKGROUND OF THE INVENTION

Some cancers may have very limited treatment options, particularly when the cancer becomes metastatic and unresectable. Despite advances in treatments such as, for example, surgery, chemotherapy, and radiation therapy, the prognosis for many cancers, such as, for example, pancreatic, colorectal, lung, endometrial, ovarian, and prostate cancers, may be poor. Accordingly, there exists an unmet need for additional treatments for cancer.

BRIEF SUMMARY OF THE INVENTION

An embodiment of the invention provides an isolated or purified T cell receptor (TCR) having antigenic specificity for mutated Kirsten rat sarcoma viral oncogene homolog (KRAS) presented in the context of a human leukocyte antigen (HLA)-Cw8 molecule.

The invention further provides related polypeptides and proteins, as well as related nucleic acids, recombinant expression vectors, host cells, populations of cells, and pharmaceutical compositions relating to the TCRs of the invention.

Methods of detecting the presence of cancer in a mammal and methods of treating or preventing cancer in a mammal are further provided by the invention.

BRIEF DESCRIPTION OF THE SEVERAL VIEWS OF THE DRAWING(S)

FIG. 1 is a graph showing the amount of interferon (IFN)-γ (pg/ml) secreted by effector T cells transduced with a nucleotide sequence encoding an anti-mutated KRAS TCR comprising the alpha chain variable region of SEQ ID NO: 9 and the beta chain variable region of SEQ ID NO: 10 upon co-culture with target dendritic cells pulsed with various concentrations (μM) of mutated $KRAS_{10-18}$ GADGVGKSA (SEQ ID NO: 18) (squares), mutated $KRAS_{9-18}$ VGADGVGKSA (SEQ ID NO: 31) (▼), mutated $KRAS_{10-19}$ GADGVGKSAL (SEQ ID NO: 30) (open circles), wild-type (WT) $KRAS_{10-18}$ GAGGVGKSA (SEQ ID NO: 17) (closed circles), WT $KRAS_{9-18}$ VGAGGVGKSA (SEQ ID NO: 32) (▲), or WT $KRAS_{10-19}$ GAGGVGKSAL (SEQ ID NO: 33) (diamonds).

DETAILED DESCRIPTION OF THE INVENTION

Kirsten rat sarcoma viral oncogene homolog (KRAS), also referred to as GTPase KRas, V-Ki-Ras2 Kirsten rat sarcoma viral oncogene, or KRAS2, is a member of the small GTPase superfamily. There are two transcript variants of KRAS: KRAS variant A and KRAS variant B. Hereinafter, references to "KRAS" (mutated or unmutated) refer to both variant A and variant B, unless specified otherwise. Without being bound to a particular theory or mechanism, it is believed that, when mutated, KRAS may be involved in signal transduction early in the oncogenesis of many human cancers. A single amino acid substitution may activate the mutation. When activated, mutated KRAS binds to guanosine-5'-triphosphate (GTP) and converts GTP to guanosine 5'-diphosphate (GDP). The mutated KRAS protein product may be constitutively activated. Mutated KRAS protein may be expressed in any of a variety of human cancers such as, for example, pancreatic (e.g., pancreatic carcinoma), colorectal, lung (e.g., lung adenocarcinoma), endometrial, ovarian (e.g., epithelial ovarian cancer), and prostate cancers.

An embodiment of the invention provides an isolated or purified TCR having antigenic specificity for mutated human KRAS (hereinafter, "mutated KRAS"). Hereinafter, references to a "TCR" also refer to functional portions and functional variants of the TCR, unless specified otherwise. The inventive TCR may have antigenic specificity for any KRAS (protein, polypeptide or peptide) with a G12D mutation. In an embodiment of the invention, the TCR has antigenic specificity for a KRAS protein with the G12D mutation, the KRAS protein comprising or consisting of the amino acid sequence of SEQ ID NO: 15 or 16. The mutated KRAS variant A protein amino acid sequence of SEQ ID NO: 15 generally corresponds to positions 1-189 of the unmutated, wild-type (WT) KRAS protein variant A amino acid sequence of SEQ ID NO: 1 with the exception that in SEQ ID NO: 15, the glycine at position 12 is substituted with aspartic acid. The mutated KRAS variant B protein amino acid sequence of SEQ ID NO: 16 generally corresponds to positions 1-188 of the unmutated, WT KRAS protein variant B amino acid sequence of SEQ ID NO: 2 with the exception that in SEQ ID NO: 16, the glycine at position 12 is substituted with aspartic acid. In an embodiment of the invention, the TCR has antigenic specificity for a KRAS peptide with the G12D mutation described above, the KRAS peptide having any length. For example, the TCR may have antigenic specificity for a KRAS peptide with the G12D mutation, the KRAS peptide having a length of about 8 to about 24 amino acid residues, preferably about 9 to about 11 amino acid residues. In an embodiment of the invention, the TCR may have antigenic specificity for a KRAS peptide with the G12D mutation, the KRAS peptide having a length of about 8 amino acid residues, about 9 amino acid residues, about 10 amino acid residues, about 11 amino acid residues, about 12 amino acid residues, or about 24 amino acid residues. For example, the TCR may have antigenic specificity for a $KRAS_{10-18}$ peptide with the G12D mutation, the peptide comprising or consisting of the amino acid sequence of GADGVGKSA (SEQ ID NO: 18). The mutated KRAS peptide amino acid sequence of SEQ ID NO: 18 with the G12D mutation generally corresponds to positions 1-9 of the unmutated, WT $KRAS_{10-18}$ peptide amino acid sequence of SEQ ID NO: 17 with the exception that in SEQ ID NO: 18, the glycine at position 3 is substituted with aspartic acid. In still another embodiment of the invention, the TCR may have antigenic specificity for a KRAS peptide with the G12D mutation, the mutated KRAS peptide comprising or consisting of the amino acid sequence of MTEYKLVVVGADGVGKSALTIQLI (SEQ ID NO: 20); GADGVGKSA (mutated $KRAS_{10-18}$; SEQ ID NO: 18); VGADGVGKSA (mutated $KRAS_{9-18}$; SEQ ID NO: 31); or GADGVGKSAL (mutated $KRAS_{10-19}$; SEQ ID NO: 30). In an exemplary embodiment, the TCR has antigenic specificity for a mutated KRAS epitope, the mutated KRAS epitope comprising or consisting of the amino acid sequence of MTEYKLVVVGADGVGKSALTIQLI (SEQ ID NO: 20); GADGVGKSA (mutated $KRAS_{10-18}$; SEQ ID NO: 18); VGADGVGKSA (mutated $KRAS_{9-18}$; SEQ ID NO: 31); or GADGVGKSAL (mutated $KRAS_{10-19}$; SEQ ID NO: 30).

In an embodiment of the invention, the inventive TCRs are able to recognize mutated KRAS in an HLA-Cw8-dependent manner. "HLA-Cw8-dependent manner," as used herein, means that the TCR elicits an immune response upon binding to mutated KRAS within the context of an HLA-Cw8 molecule. The inventive TCRs are able to recognize mutated KRAS that is presented by an HLA-Cw8 molecule and may bind to the HLA-Cw8 molecule in addition to mutated KRAS. Exemplary HLA-Cw8 molecules, in the context of which the inventive TCRs recognize mutated KRAS, include those encoded by the HLA-Cw*0801, HLA-Cw*0802, HLA-Cw*0803, HLA-Cw*0804, HLA-Cw*0805, HLA-Cw*0806, HLA-Cw*0807, HLA-Cw*0808, and HLA-Cw*0809 alleles. In a preferred embodiment, the TCRs recognize mutated KRAS within the context of an HLA-Cw*0802 molecule.

The TCRs of the invention provide many advantages, including when expressed by cells used for adoptive cell transfer. Mutated KRAS is expressed by cancer cells and is not expressed by normal, noncancerous cells. Without being bound to a particular theory or mechanism, it is believed that the inventive TCRs advantageously target the destruction of cancer cells while minimizing or eliminating the destruction of normal, non-cancerous cells, thereby reducing, for example, by minimizing or eliminating, toxicity. Moreover, the inventive TCRs may, advantageously, successfully treat or prevent mutated KRAS-positive cancers that do not respond to other types of treatment such as, for example, chemotherapy, surgery, or radiation. Additionally, the inventive TCRs may provide highly avid recognition of mutated KRAS, which may provide the ability to recognize unmanipulated tumor cells (e.g., tumor cells that have not been treated with interferon (IFN)-γ, transfected with a vector encoding one or both of mutated KRAS and HLA-Cw*0802, pulsed with a KRAS peptide with the G12D mutation, or a combination thereof). Moreover, the HLA-Cw*0802 allele is expressed in up to about 8% and about 11% of American Caucasian and African American ethnicities, respectively. Accordingly, the inventive TCRs may increase the number of immunotherapy-eligible cancer patients to include those patients that express the HLA-Cw*0802 allele who may not be eligible for immunotherapy using TCRs that recognize antigen in the context of other MHC molecules.

The phrase "antigenic specificity," as used herein, means that the TCR can specifically bind to and immunologically recognize mutated KRAS with high avidity. For example, a TCR may be considered to have "antigenic specificity" for mutated KRAS if about $1\times10^4$ to about $1\times10^5$ T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative HLA-Cw*0802$^+$ target cells pulsed with a low concentration of mutated KRAS peptide (e.g., about 0.05 ng/mL to about 5 ng/mL, 0.05 ng/mL, 0.1 ng/mL, 0.5 ng/mL, 1 ng/mL, 5 ng/mL, or a range defined by any two of the foregoing values) or (b) antigen-negative HLA-Cw*0802$^+$ target cells into which a nucleotide sequence encoding mutated KRAS has been introduced such that the target cell expresses mutated KRAS. Cells expressing the inventive TCRs may also secrete IFN-γ upon co-culture with antigen-negative HLA-Cw*0802$^+$ target cells pulsed with higher concentrations of mutated KRAS peptide.

Alternatively or additionally, a TCR may be considered to have "antigenic specificity" for mutated KRAS if T cells expressing the TCR secrete at least twice as much IFN-γ upon co-culture with (a) antigen-negative HLA-Cw*0802$^+$ target cells pulsed with a low concentration of mutated KRAS peptide or (b) antigen-negative HLA-Cw*0802$^+$ target cells into which a nucleotide sequence encoding mutated KRAS has been introduced such that the target cell expresses mutated KRAS as compared to the amount of IFN-γ expressed by a negative control. The negative control may be, for example, (i) T cells expressing the TCR, co-cultured with (a) antigen-negative HLA-Cw*0802$^+$ target cells pulsed with the same concentration of an irrelevant peptide (e.g., some other peptide with a different sequence from the mutated KRAS peptide) or (b) antigen-negative HLA-Cw*0802$^+$ target cells into which a nucleotide sequence encoding an irrelevant peptide has been introduced such that the target cell expresses the irrelevant peptide, or (ii) untransduced T cells (e.g., derived from PBMC, which do not express the TCR) co-cultured with (a) antigen-negative HLA-Cw*0802$^+$ target cells pulsed with the same concentration of mutated KRAS peptide or (b) antigen-negative HLA-Cw*0802$^+$ target cells into which a nucleotide sequence encoding mutated KRAS has been introduced such that the target cell expresses mutated KRAS. IFN-γ secretion may be measured by methods known in the art such as, for example, enzyme-linked immunosorbent assay (ELISA).

Alternatively or additionally, a TCR may be considered to have "antigenic specificity" for mutated KRAS if at least twice as many of the numbers of T cells expressing the TCR secrete IFN-γ upon co-culture with (a) antigen-negative HLA-Cw*0802$^+$ target cells pulsed with a low concentration of mutated KRAS peptide or (b) antigen-negative HLA-Cw*0802$^+$ target cells into which a nucleotide sequence encoding mutated KRAS has been introduced such that the target cell expresses mutated KRAS as compared to the numbers of negative control T cells that secrete IFN-γ. The concentration of peptide and the negative control may be as described herein with respect to other aspects of the invention. The numbers of cells secreting IFN-γ may be measured by methods known in the art such as, for example, ELISPOT.

Alternatively or additionally, a TCR may be considered to have "antigenic specificity" for mutated KRAS if T cells expressing the TCR upregulate expression of one or both of 4-1BB and OX40 as measured by, for example, flow cytometry after stimulation with target cells expressing mutated KRAS.

The invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for mutated KRAS.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 3 (CDR1 of α chain), a CDR2 comprising the amino acid sequence of SEQ ID NO: 4 (CDR2 of α chain), and a CDR3 comprising the amino acid sequence of SEQ ID NO: 5 (CDR3 of α chain), and a second polypeptide chain comprising a CDR1 comprising the amino acid sequence of SEQ ID NO: 6 (CDR1 of β chain), a CDR2 comprising the amino acid sequence of SEQ ID NO: 7 (CDR2 of β chain), and a CDR3 comprising the amino acid sequence of SEQ ID NO: 8 (CDR3 of β chain). In this regard, the inventive TCR can comprise any one or more of the amino acid sequences selected from the group consisting of SEQ ID NOs: 3-8. Preferably, the TCR comprises the amino acid sequences of SEQ ID NOs: 3-5 or SEQ ID NOs: 6-8. In an especially preferred embodiment, the TCR comprises the amino acid sequences of all of SEQ ID NOs: 3-8.

In an embodiment of the invention, the TCR comprises an amino acid sequence of a variable region of a TCR comprising the CDRs set forth above. In this regard, the TCR can comprise the amino acid sequence of SEQ ID NO: 9 (variable region of α chain); SEQ ID NO: 10 (variable region of β chain); or both SEQ ID NOs: 9 and 10. Preferably, the inventive TCR comprises the amino acid sequences of both SEQ ID NOs: 9 and 10.

The inventive TCRs may further comprise a constant region. The constant region may be derived from any suitable species such as, e.g., human or mouse. In an embodiment of the invention, the TCRs further comprise a murine constant region. As used herein, the term "murine" or "human," when referring to a TCR or any component of a TCR described herein (e.g., complementarity determining region (CDR), variable region, constant region, alpha chain, and/or beta chain), means a TCR (or component thereof) which is derived from a mouse or a human, respectively, i.e., a TCR (or component thereof) that originated from or was, at one time, expressed by a mouse T cell or a human T cell, respectively.

An embodiment of the invention provides a chimeric TCR comprising a human variable region and a murine constant region, wherein the TCR has antigenic specificity for mutated KRAS presented in the context of an HLA-Cw8 molecule. The chimeric TCR may comprise the amino acid sequence of SEQ ID NO: 24 (wild-type (WT) murine α chain constant region), SEQ ID NO: 25 (WT murine β chain constant region), or both SEQ ID NOs: 24 and 25. Preferably, the inventive TCR comprises the amino acid sequences of both SEQ ID NOs: 24 and 25. The chimeric TCR may comprise any of the CDR regions as described herein with respect to other aspects of the invention. In another embodiment of the invention, the chimeric TCR may comprise any of the variable regions described herein with respect to other aspects of the invention. In this regard, the chimeric TCR may comprise the amino acid sequences of (i) SEQ ID NOs: 3-5 and 24; (ii) SEQ ID NOs: 6-8 and 25; (iii) SEQ ID NOs: 3-8 and 24-25; (iv) SEQ ID NO: 9 and 24; (v) SEQ ID NO: 10 and 25; or (vi) SEQ ID NOs: 9-10 and 24-25. Preferably, the chimeric TCR comprises the amino acid sequences of (i) SEQ ID NOs: 3-8 and 24-25 or (ii) SEQ ID NOs: 9-10 and 24-25.

In an embodiment of the invention, the inventive TCR can comprise an α chain of a TCR and a β chain of a TCR. Each of the α chain and β chain of the inventive TCR can independently comprise any amino acid sequence. In this regard, the α chain of the inventive chimeric TCR can comprise the amino acid sequence of SEQ ID NO: 26. An α chain of this type can be paired with any β chain of a TCR. In this regard, the β chain of the inventive TCR can comprise the amino acid sequence of SEQ ID NO: 27. The inventive TCR, therefore, can comprise the amino acid sequence of SEQ ID NO: 26, SEQ ID NO: 27, or both SEQ ID NOs: 26 and 27. Preferably, the inventive TCR comprises the amino acid sequences of both SEQ ID NOs: 26 and 27.

In an embodiment of the invention, the TCR comprises a substituted constant region. In this regard, the TCR may comprise the amino acid sequence of any of the TCRs described herein with one, two, three, or four amino acid substitution(s) in the constant region of one or both of the alpha and beta chain. In some embodiments, the TCRs comprising the substituted constant region advantageously provide one or more of increased recognition of mutated $KRAS^+$ targets, increased expression by a host cell, and increased anti-tumor activity as compared to the parent TCR comprising an unsubstituted (wild-type) constant region. In general, the substituted amino acid sequences of the murine constant regions of the TCR α and β chains, SEQ ID NOs: 11 and 12, respectively, correspond with all or portions of the unsubstituted murine constant region amino acid sequences SEQ ID NOs: 24 and 25, respectively, with SEQ ID NO: 11 having one, two, three, or four amino acid substitution(s) when compared to SEQ ID NO: 24 and SEQ ID NO: 12 having one amino acid substitution when compared to SEQ ID NO: 25. In this regard, an embodiment of the invention provides a TCR comprising the amino acid sequences of (a) SEQ ID NO: 11 (constant region of alpha chain), wherein (i) X at position 48 is Thr or Cys; (ii) X at position 112 is Ser, Ala, Val, Leu, Ile, Pro, Phe, Met, or Trp; (iii) X at position 114 is Met, Ala, Val, Leu, Ile, Pro, Phe, or Trp; and (iv) X at position 115 is Gly, Ala, Val, Leu, Ile, Pro, Phe, Met, or Trp; and (b) SEQ ID NO: 12 (constant region of beta chain), wherein X at position 57 is Ser or Cys. In an embodiment of the invention, the TCR comprising SEQ ID NO: 11 does not comprise SEQ ID NO: 24 (unsubstituted murine constant region of alpha chain). In an embodiment of the invention, the TCR comprising SEQ ID NO: 12 does not comprise SEQ ID NO: 25 (unsubstituted murine constant region of beta chain).

In an embodiment of the invention, the substituted constant region includes cysteine substitutions in the constant region of one or both of the α and β chains to provide a cysteine-substituted TCR. Opposing cysteines in the α and the β chains provide a disulfide bond that links the constant regions of the α and the β chains of the substituted TCR to one another and which is not present in a TCR comprising the unsubstituted murine constant regions. In this regard, the TCR may be a cysteine-substituted, chimeric TCR in which one or both of the native Thr48 of SEQ ID NO: 24 and the native Ser57 of SEQ ID NO: 25 may be substituted with Cys. Preferably, both of the native Thr48 of SEQ ID NO: 24 and the native Ser57 of SEQ ID NO: 25 are substituted with Cys. In an embodiment, the cysteine-substituted, chimeric TCR comprises an alpha chain constant region comprising the amino acid sequence of SEQ ID NO: 11, wherein X at position 48 is Cys, X at position 112 is the native Ser, X at position 114 is the native Met, and X at position 115 is the native Gly, and a beta chain constant region comprising the amino acid sequence of SEQ ID NO: 12, wherein X at position 57 is Cys. The cysteine-substituted, chimeric TCRs of the invention may include the substituted constant region in addition to any of the CDRs and/or variable regions described herein. In this regard, the cysteine-substituted, chimeric TCR can comprise the amino acid sequences of (i) SEQ ID NOs: 3-8 and 11-12; (ii) SEQ ID NOs: 9-12; (iii) SEQ ID NOs: 3-5 and 11; (iv) SEQ ID NOs: 6-8 and 12; (v) SEQ ID NOs: 9 and 11; or (vi) SEQ ID NOs: 10 and 12. Preferably, the cysteine-substituted, chimeric TCR comprises the amino acid sequences of (i) SEQ ID NOs: 3-8 and 11-12 or (ii) SEQ ID NOs: 9-12.

In an embodiment of the invention, the cysteine-substituted, chimeric TCR comprises a full length alpha chain and a full-length beta chain. In this regard, the TCR may be a cysteine-substituted, chimeric TCR in which one or both of the native Thr177 of SEQ ID NO: 26 and the native Ser189 of SEQ ID NO: 27 may be substituted with Cys. Preferably, both of the native Thr177 of SEQ ID NO: 26 and the native Ser189 of SEQ ID NO: 27 are substituted with Cys. In an embodiment, the cysteine-substituted, chimeric TCR comprises an alpha chain comprising the amino acid sequence of SEQ ID NO: 13, wherein X at position 177 is Cys, X at position 241 is the native Ser, X at position 243 is the native Met, and X at position 244 is the native Gly, and a beta chain constant region comprising the amino acid sequence of SEQ ID NO: 14, wherein X at position 189 is Cys. In this regard, the cysteine-substituted, chimeric TCR may comprise the amino acid sequence of (i) SEQ ID NO: 13, (ii) SEQ ID NO: 14, or (iii) both SEQ ID NOs: 13-14. Preferably, the cysteine-substituted, chimeric TCR comprises a full length alpha chain comprising the amino acid sequence of SEQ ID NO: 13 and a full-length beta chain comprising the amino acid sequence of SEQ ID NO: 14.

In an embodiment of the invention, the substituted amino acid sequence includes substitutions of one, two, or three amino acids in the transmembrane (TM) domain of the constant region of one or both of the α and β chains with a hydrophobic amino acid to provide a hydrophobic amino acid-substituted TCR (also referred to herein as an "LVL-modified TCR"). The hydrophobic amino acid substitution(s) in the TM domain of the TCR may increase the hydrophobicity of the TM domain of the TCR as compared to a TCR that lacks the hydrophobic amino acid substitution(s) in the TM domain. In this regard, the TCR is an LVL-modified chimeric TCR in which one, two, or three of the native Ser112, Met114, and Gly115 of SEQ ID NO: 24 may, independently, be substituted with Ala, Val, Leu, Ile, Pro, Phe, Met, or Trp; preferably with Leu, Ile, or Val. Preferably, all three of the native Ser112, Met114, and Gly115 of SEQ ID NO: 24 may, independently, be substituted with Ala, Val, Leu, Ile, Pro, Phe, Met, or Trp; preferably with Leu, Ile, or Val. In an embodiment, the LVL-modified chimeric TCR comprises an alpha chain constant region comprising the amino acid sequence of SEQ ID NO: 11, wherein X at position 48 is the native Thr, X at position 112 is Ser, Ala, Val, Leu, Ile, Pro, Phe, Met, or Trp, X at position 114 is Met, Ala, Val, Leu, Ile, Pro, Phe, or Trp, and X at position 115 is Gly, Ala, Val, Leu, Ile, Pro, Phe, Met, or Trp, and a beta chain constant region comprising the amino acid sequence of SEQ ID NO: 25, wherein the LVL-modified chimeric TCR comprising SEQ ID NO: 11 does not comprise SEQ ID NO: 24 (unsubstituted murine constant region of alpha chain). In a preferred embodiment, the LVL-modified chimeric TCR comprises an alpha chain constant region comprising the amino acid sequence of SEQ ID NO: 11, wherein X at position 48 is the native Thr, X at position 112 is Leu, X at position 114 is Ile, and X at position 115 is Val, and a beta chain constant region comprising the amino acid sequence of SEQ ID NO: 25. Preferably, the LVL-modified, chimeric TCR comprises an alpha chain constant region comprising the amino acid sequence of SEQ ID NO: 11 and a beta chain constant region comprising the amino acid sequence of SEQ ID NO: 25. The LVL-modified, chimeric TCRs of the invention may include the substituted constant region in addition to any of the CDRs and/or variable regions described herein. In this regard, the LVL-modified, chimeric TCR can comprise the amino acid sequences of (i) SEQ ID NOs: 3-5 and 11; (ii) SEQ ID NOs: 6-8 and 25; (iii) SEQ ID NOs: 3-8 and 11 and 25; (iv) SEQ ID NOs: 9 and 11; (v) SEQ ID NOs: 10 and 25; or (vi) SEQ ID NOs: 9-11 and 25. Preferably, the LVL-modified, chimeric TCR comprises the amino acid sequences of (i) SEQ ID NOs: 3-8, 11, and 25 or (ii) SEQ ID NOs: 9-11 and 25.

In an embodiment of the invention, the LVL-modified TCR comprises a full length alpha chain and a full-length beta chain. In this regard, the TCR may be an LVL-modified chimeric TCR in which one, two, or three of the native Ser241, Met243, and Gly244 of SEQ ID NO: 26 may, independently, be substituted with Ala, Val, Leu, Ile, Pro, Phe, Met, or Trp; preferably with Leu, Ile, or Val. Preferably, all three of the native Ser241, Met243, and Gly244 of SEQ ID NO: 26 may, independently, be substituted with Ala, Val, Leu, Ile, Pro, Phe, Met, or Trp; preferably with Leu, Ile, or Val. In an embodiment, the LVL-modified chimeric TCR comprises an alpha chain comprising the amino acid sequence of SEQ ID NO: 13, wherein X at position 177 is the native Thr, X at position 241 is Ser, Ala, Val, Leu, Ile, Pro, Phe, Met, or Trp, X at position 243 is Met, Ala, Val, Leu, Ile, Pro, Phe, or Trp, and X at position 244 is Gly, Ala, Val, Leu, Ile, Pro, Phe, Met, or Trp, and a beta chain comprising the amino acid sequence of SEQ ID NO: 27, wherein the LVL-modified chimeric TCR comprising SEQ ID NO: 13 does not comprise SEQ ID NO: 26 (unsubstituted murine alpha chain). In a preferred embodiment, the LVL-modified chimeric TCR comprises an alpha chain comprising the amino acid sequence of SEQ ID NO: 13, wherein X at position 177 is the native Thr, X at position 241 is Leu, X at position 243 is Ile, and X at position 244 is Val, and a beta chain comprising the amino acid sequence of SEQ ID NO: 27, wherein the LVL-modified chimeric TCR comprising SEQ ID NO: 13 does not comprise SEQ ID NO: 26 (unsubstituted murine alpha chain). Preferably, the LVL-modified, chimeric TCR comprises an alpha chain comprising the amino acid sequence of SEQ ID NO: 13 and a beta chain constant region comprising the amino acid sequence of SEQ ID NO: 27.

In an embodiment of the invention, the substituted amino acid sequence includes the cysteine substitutions in the constant region of one or both of the α and β chains in combination with the substitution(s) of one, two, or three amino acids in the transmembrane (TM) domain of the constant region of one or both of the α and β chains with a hydrophobic amino acid (also referred to herein as "cysteine-substituted, LVL-modified TCR"). In this regard, the TCR is a cysteine-substituted, LVL-modified, chimeric TCR in which the native Thr48 of SEQ ID NO: 24 is substituted with Cys; one, two, or three of the native Ser112, Met114, and Gly115 of SEQ ID NO: 24 are, independently, substituted with Ala, Val, Leu, Ile, Pro, Phe, Met, or Trp; preferably with Leu, Ile, or Val; and the native Ser57 of SEQ ID NO: 25 is substituted with Cys. Preferably, all three of the native Ser112, Met114, and Gly115 of SEQ ID NO: 24 may, independently, be substituted with Ala, Val, Leu, Ile, Pro, Phe, Met, or Trp; preferably with Leu, Ile, or Val. In an embodiment, the cysteine-substituted, LVL-modified, chimeric TCR comprises an alpha chain comprising the amino acid sequence of SEQ ID NO: 11, wherein X at position 48 is Cys, X at position 112 is Ser, Ala, Val, Leu, Ile, Pro, Phe, Met, or Trp, X at position 114 is Met, Ala, Val, Leu, Ile, Pro, Phe, or Trp, and X at position 115 is Gly, Ala, Val, Leu, Ile, Pro, Phe, Met, or Trp, and a beta chain comprising the amino acid sequence of SEQ ID NO: 12, wherein X at position 57 is Cys, wherein SEQ ID NO: 11 does not comprise SEQ ID NO: 24 (unsubstituted alpha chain) and SEQ ID NO: 12 does not comprise SEQ ID NO: 25 (unsubstituted beta chain). Preferably, the cysteine-substituted, LVL-modified, chimeric TCR comprises an alpha chain comprising the amino acid sequence of SEQ ID NO: 11, wherein X at position 48 is Cys, X at position 112 is Leu, X at position 114 is Ile, X at position 115 is Val, and a beta chain comprising the amino acid sequence of SEQ ID NO: 12, wherein X at position 57 is Cys. The cysteine-substituted, LVL-modified, chimeric TCRs of the invention may include the substituted constant region in addition to any of the CDRs and/or variable regions described herein. In this regard, the cysteine-substituted, LVL-modified, chimeric TCR can comprise (i) SEQ ID NOs: 3-5 and 11; (ii) SEQ ID NO: 9 and 11; (iii) SEQ ID NOs: 6-8 and 12; (iv) SEQ ID NO: 10 and 12; (v) SEQ ID NOs: 3-8 and 11-12; or (vi) SEQ ID NOs: 9-12. Preferably, the cysteine-substituted, LVL-modified, chimeric TCR comprises the amino acid sequences of (i) SEQ ID NOs: 3-8 and 11-12 or (ii) SEQ ID NOs: 9-12.

In an embodiment, the cysteine-substituted, LVL-modified, chimeric TCR comprises a full-length alpha chain and a full-length beta chain. In this regard, the TCR may be a cysteine-substituted, LVL-modified, chimeric TCR in which the native Thr177 of SEQ ID NO: 26 is substituted with Cys and one, two, or three of the native Ser241, Met243, and Gly244 of SEQ ID NO: 26 may, independently, be substituted with Ala, Val, Leu, Ile, Pro, Phe, Met, or Trp; preferably with Leu, Ile, or Val. Preferably, all three of the native Ser241, Met243, and Gly244 of SEQ ID NO: 26 may, independently, be substituted with Ala, Val, Leu, Ile, Pro, Phe, Met, or Trp; preferably with Leu, Ile, or Val. In an embodiment, the cysteine-substituted, LVL-modified, chimeric TCR comprises an alpha chain comprising the amino acid sequence of SEQ ID NO: 13, wherein X at position 177 is Cys, X at position 241 is Ser, Ala, Val, Leu, Ile, Pro, Phe, Met, or Trp, X at position 243 is Met, Ala, Val, Leu, Ile, Pro, Phe, or Trp, and X at position 244 is Gly, Ala, Val, Leu, Ile, Pro, Phe, Met, or Trp, and a beta chain comprising the amino acid sequence of SEQ ID NO: 14, wherein X at position 189 is Cys, wherein the cysteine-substituted, LVL-modified, chimeric comprising SEQ ID NO: 13 does not comprise SEQ ID NO: 26 (unsubstituted murine alpha chain). In a preferred embodiment, the cysteine-substituted, LVL-modified, chimeric TCR comprises an alpha chain comprising the amino acid sequence of SEQ ID NO: 13, wherein X at position 177 is Cys, X at position 241 is Leu, X at position 243 is Ile, and X at position 244 is Val, and a beta chain comprising the amino acid sequence of SEQ ID NO: 14, wherein X at position 189 is Cys.

Included in the scope of the invention are functional variants of the inventive TCRs described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to mutated KRAS for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein, respectively.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein. In this regard, the inventive TCR, polypeptide, or protein can, for example, consist essentially of the amino acid sequence of SEQ ID NO: 26, SEQ ID NO: 27, both SEQ ID NOs: 26 and 27, SEQ ID NO: 13, SEQ ID NO: 14, SEQ ID NOs: 13-14, or both SEQ ID NOs: 13 and 27, wherein SEQ ID NOs: 13 and 14 are substituted as described herein with respect to other aspects of the invention. Also, for instance, the inventive TCRs, polypeptides, or proteins can consist essentially of the amino acid sequence(s) of SEQ ID NO: 9, SEQ ID NO: 10, or both SEQ ID NOs: 9 and 10. Furthermore, the inventive TCRs, polypeptides, or proteins can consist essentially of the amino acid sequence of SEQ ID NO: 3 (CDR1 of α chain), SEQ ID NO: 4 (CDR2 of α chain), SEQ ID NO: 5 (CDR3 of α chain), SEQ ID NO: 6 (CDR1 of β chain), SEQ ID NO: 7 (CDR2 of β chain), SEQ ID NO: 8 (CDR3 of β chain), or any combination thereof, e.g., SEQ ID NOs: 3-5; 6-8; or 3-8.

Also provided by the invention is a polypeptide comprising a functional portion of any of the TCRs described herein. The term "polypeptide," as used herein, includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to mutated KRAS. The term "functional portion," when used in reference to a TCR, refers to any part or fragment of the TCR of the invention, which part or fragment retains the biological activity of the TCR of which it is a part (the parent TCR). Functional portions encompass, for example, those parts of a TCR that retain the ability to specifically bind to mutated KRAS (e.g., in an HLA-Cw*0802-dependent manner), or detect, treat, or prevent cancer, to a similar extent, the same extent, or to a higher extent, as the parent TCR. In reference to the parent TCR, the functional portion can comprise, for instance, about 10%, 25%, 30%, 50%, 68%, 80%, 90%, 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to mutated KRAS; and/or having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one of more of CDR1, CDR2, and CDR3 of the variable region(s) of the α chain and/or β chain of a TCR of the invention. In an embodiment of the invention, the polypeptide can comprise a functional portion comprising the amino acid sequence of SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), or a combination thereof. Preferably, the inventive polypeptide comprises a functional portion comprising the amino acid sequences of SEQ ID NOs: 3-5; 6-8; or all of SEQ ID NOs: 3-8. More preferably, the polypeptide comprises a functional portion comprising the amino acid sequences of all of SEQ ID NOs: 3-8.

In an embodiment of the invention, the inventive polypeptide can comprise, for instance, the variable region of the inventive TCR comprising a combination of the CDR regions set forth above. In this regard, the polypeptide can comprise the amino acid sequence of SEQ ID NO: 9 (variable region of α chain), SEQ ID NO: 10 (variable region of β chain), or both SEQ ID NOs: 9 and 10. Preferably, the polypeptide comprises the amino acid sequences of both SEQ ID NOs: 9 and 10.

In an embodiment of the invention, the inventive polypeptide can further comprise the constant region of the inventive TCR set forth above. In this regard, the polypeptide can comprise the amino acid sequence of SEQ ID NO: 24 (WT murine constant region of α chain), SEQ ID NO: 25 (WT murine constant region of (chain), SEQ ID NO: 11 (murine constant region of α chain), SEQ ID NO: 12 (murine constant region of β chain), both SEQ ID NOs: 11 and 25, both SEQ ID NOs: 11 and 12, or both SEQ ID NOs: 24 and 25, wherein SEQ ID NOs: 11 and 12 are substituted as described herein with respect to other aspects of the invention. Preferably, the polypeptide comprises the amino acid sequences of both (i) SEQ ID NOs: 11 and 12, (ii) SEQ ID NOs: 24 and 25, or (iii) SEQ ID NOs: 11 and 25, wherein SEQ ID NOs: 11 and 12 are substituted as described herein with respect to other aspects of the invention.

In an embodiment of the invention, the inventive polypeptide may comprise a combination of a variable region and a constant region of the inventive TCR. In this regard, the polypeptide can comprise the amino acid sequences of (i) both SEQ ID NO: 9 (variable region of α chain) and SEQ ID NO: 24 (constant region of α chain), (ii) both SEQ ID NO: 10 (variable region of β chain) and SEQ ID NO: 25 (constant region of β chain), (iii) all of SEQ ID NOs: 9, 10, 24, and 25, (iv) both SEQ ID NOs: 9 and 11, (v) both SEQ ID NOs: 10 and 12, (vi) all of SEQ ID NOs: 9-12, or (vii) SEQ ID NOs: 9-11 and 25, wherein SEQ ID NOs: 11 and 12 are substituted as described herein with respect to other aspects of the invention. Preferably, the polypeptide comprises the amino acid sequences of (i) all of SEQ ID NOs: 9, 10, 24, and 25, (ii) all of SEQ ID NOs: 9-12, wherein SEQ ID NOs: 11 and 12, or (iii) all of SEQ ID NOs: 9-11 and 25, wherein SEQ ID NOs: 11-12 are substituted as described herein with respect to other aspects of the invention.

In an embodiment of the invention, the inventive polypeptide may comprise a combination of any of the CDR regions described herein and a constant region of the inventive TCR. In this regard, the polypeptide can comprise the amino acid sequences of (i) all of SEQ ID NOs: 3-5 and 24, (ii) all of SEQ ID NOs: 6-8 and 25, (iii) all of SEQ ID NOs: 3-8 and 24-25; (iv) all of SEQ ID NOs: 3-5 and 11; (v) all of SEQ ID NOs: 6-8 and 12; (vi) all of SEQ ID NOs: 3-8 and 11-12, or (vii) all of SEQ ID NOs: 3-5, 11, and 25, wherein SEQ ID NOs: 11 and 12 are substituted as described herein with respect to other aspects of the invention. Preferably, the polypeptide comprises the amino acid sequences of (i) all of SEQ ID NOs: 3-8 and 24-25, (ii) all of SEQ ID NOs: 3-8 and 11-12, or (iii) all of SEQ ID NOs: 3-5, 11, and 25, wherein SEQ ID NOs: 11 and 12 are substituted as described herein with respect to other aspects of the invention.

In an embodiment of the invention, the inventive polypeptide can comprise the entire length of an α or β chain of the TCR described herein. In this regard, the inventive polypeptide can comprise the amino acid sequence of (i) SEQ ID NO: 26, (ii) SEQ ID NO: 27, (iii) both SEQ ID NOs: 26 and 27, (iv) SEQ ID NO: 13, (v) SEQ ID NO: 14, (vi) both SEQ ID NOs: 13 and 14, (vii) both SEQ ID NOs: 13 and 27, wherein SEQ ID NOs: 13 and 14 are substituted as described herein with respect to other aspects of the invention. Preferably, the polypeptide comprises the amino acid sequences of (i) both SEQ ID NOs: 26 and 27, (ii) both SEQ ID NOs: 13 and 14, (iii) both SEQ ID NOs: 13 and 27, wherein SEQ ID NOs: 13 and 14 are substituted as described herein with respect to other aspects of the invention.

The invention further provides a protein comprising at least one of the polypeptides described herein. By "protein" is meant a molecule comprising one or more polypeptide chains.

In an embodiment, the protein of the invention can comprise (I) a first polypeptide chain comprising the amino acid sequences of SEQ ID NOs: 3-5; (II) a second polypeptide chain comprising the amino acid sequence of SEQ ID NOs: 6-8; or (III) both (I) and (II). Alternatively or additionally, the protein of the invention can comprise (I) a first polypeptide chain comprising the amino acid sequence of SEQ ID NO: 9; (II) a second polypeptide chain comprising the amino acid sequence of SEQ ID NO: 10; or (III) (both I) and (II). The protein can, for example, comprise a first polypeptide chain comprising the amino acid sequences of both (i) SEQ ID NOs: 9 and 24, (ii) SEQ ID NOs: 9 and 11, (iii) all of SEQ ID NOs: 3-5 and 24, or (iv) all of SEQ ID NOs: 3-5 and 11 and a second polypeptide chain comprising the amino acid sequences of (i) both SEQ ID NOs: 10 and 25, (ii) SEQ ID NOs: 10 and 12, (iii) all of SEQ ID NOs: 6-8 and 25, or (iv) SEQ ID NOs: 6-8 and 12, wherein SEQ ID NOs: 11 and 12 are substituted as described herein with respect to other aspects of the invention. Alternatively or additionally, the protein of the invention can comprise a first polypeptide chain comprising the amino acid sequence of SEQ ID NO: 26 or 13 and a second polypeptide chain comprising the amino acid sequence of SEQ ID NO: 27 or 14, wherein SEQ ID NOs: 13 and 14 are substituted as described herein with respect to other aspects of the invention. In this instance, the protein of the invention can be a TCR. Alternatively, if, for example, the protein comprises a single polypeptide chain comprising the amino acid sequences of both SEQ ID NOs: 26 and 27 or both SEQ ID NOs: 13 and 14, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs, polypeptides, and proteins of the invention may be expressed as a single protein comprising a linker peptide linking the α chain and the β chain. In this regard, the TCRs, polypeptides, and proteins of the invention may further comprise a linker peptide. The linker peptide may advantageously facilitate the expression of a recombinant TCR, polypeptide, and/or protein in a host cell. The linker peptide may comprise any suitable amino acid sequence. For example, the linker peptide may comprise SEQ ID NO: 23. Upon expression of the construct including the linker peptide by a host cell, the linker peptide may be cleaved, resulting in separated α and β chains. In an embodiment of the invention, the TCR, polypeptide, or protein may comprise an amino acid sequence comprising a full-length α chain, a full-length β chain, and a linker peptide positioned between the α and β chains.

The protein of the invention can be a recombinant antibody, or an antigen binding portion thereof, comprising at least one of the inventive polypeptides described herein. As used herein, "recombinant antibody" refers to a recombinant (e.g., genetically engineered) protein comprising at least one of the polypeptides of the invention and a polypeptide chain of an antibody, or an antigen binding portion thereof. The polypeptide of an antibody, or antigen binding portion thereof, can be a heavy chain, a light chain, a variable or constant region of a heavy or light chain, a single chain variable fragment (scFv), or an Fc, Fab, or $F(ab)_2'$ fragment of an antibody, etc. The polypeptide chain of an antibody, or an antigen binding portion thereof, can exist as a separate polypeptide of the recombinant antibody. Alternatively, the polypeptide chain of an antibody, or an antigen binding portion thereof, can exist as a polypeptide, which is expressed in frame (in tandem) with the polypeptide of the invention. The polypeptide of an antibody, or an antigen binding portion thereof, can be a polypeptide of any antibody or any antibody fragment, including any of the antibodies and antibody fragments described herein.

The TCRs, polypeptides, and proteins of the invention can be of any length, i.e., can comprise any number of amino acids, provided that the TCRs, polypeptides, or proteins retain their biological activity, e.g., the ability to specifically bind to mutated KRAS; detect cancer in a mammal; or treat or prevent cancer in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, amninomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A Laboratory Manual,* 4th ed., Cold Spring Harbor Press, Cold Spring Harbor, N.Y. (2012). Alternatively, the TCRs, polypeptides, and/or proteins described herein can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

An embodiment of the invention provides a nucleic acid comprising a nucleotide sequence encoding any of the TCRs, polypeptides, or proteins described herein. "Nucleic acid," as used herein, includes "polynucleotide," "oligonucleotide," and "nucleic acid molecule," and generally means a polymer of DNA or RNA, which can be single-stranded or double-stranded, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, or proteins described herein. In an embodiment of the invention, the nucleic acid may comprise the nucleotide sequences of SEQ ID NO: 28 (variable region of alpha chain) and SEQ ID NO: 29 (variable region of beta chain).

In an embodiment of the invention, the nucleic acid comprises a codon-optimized nucleotide sequence encoding any of the TCRs, polypeptides, or proteins described herein. Without being bound to any particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. In this regard, the nucleic acid may consist essentially of any of the nucleotide sequences described herein.

The nucleic acids of the invention can be incorporated into a recombinant expression vector. In this regard, the invention provides a recombinant expression vector comprising any of the nucleic acids of the invention. In an embodiment of the invention, the recombinant expression vector comprises a nucleotide sequence encoding the α chain, the β chain, and linker peptide.

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fennentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector.

The recombinant expression vectors of the invention can be prepared using standard recombinant DNA techniques described in, for example, Green and Sambrook et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein, or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5a cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD4^+$ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.,* 26:332-42 (2003); and Riddell et al., *J. Immunol. Methods,* 128:189-201 (1990). In an embodiment, expansion of the numbers of T cells is carried out by culturing the T cells with OKT3 antibody, IL-2, and feeder PBMC (e.g., irradiated allogeneic PBMC).

The inventive TCRs, polypeptides, proteins, nucleic acids, recombinant expression vectors, and host cells (including populations thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins, nucleic acids, recombinant expression vectors, and host cells (including populations thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, nucleic acids, expression vectors, and host cells (including populations thereof), described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Methods for preparing administrable compositions are known or apparent to those skilled in the art and are described in more detail in, for example, *Remington: The Science and Practice of Pharmacy,* $22^{nd}$ Ed., Pharmaceutical Press (2012). It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., mutated KRAS), or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which each is given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1\times10^6$ to about $1\times10^{12}$ cells or more. In certain embodiments, fewer than $1\times10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive inventive TCR materials can be conjugated either directly or indirectly through a bridge to a chemotherapeutic agent. The practice of conjugating compounds to a chemotherapeutic agent is known in the art. One of ordinary skill in the art recognizes that sites on the inventive TCR materials, which are not necessary for the function of the inventive TCR materials, are ideal sites for attaching a bridge and/or a chemotherapeutic agent, provided that the bridge and/or chemotherapeutic agent, once attached to the inventive TCR materials, do(es) not interfere with the function of the inventive TCR materials, i.e., the ability to bind to mutated KRAS or to detect, treat, or prevent cancer.

It is contemplated that the inventive pharmaceutical compositions, TCRs, polypeptides, proteins, nucleic acids, recombinant expression vectors, host cells, or populations of cells can be used in methods of treating or preventing cancer. Without being bound to a particular theory, the inventive TCRs are believed to bind specifically to mutated KRAS, such that the TCR (or related inventive polypeptide or protein), when expressed by a cell, is able to mediate an immune response against a target cell expressing mutated KRAS. In this regard, the invention provides a method of treating or preventing cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, for use in the treatment or prevention of cancer in a mammal.

The terms “treat,” and “prevent” as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, “prevention” can encompass delaying the onset of the cancer, or a symptom or condition thereof. Alternatively or additionally, “prevention” may encompass preventing or delaying the recurrence of cancer, or a symptom or condition thereof.

Also provided is a method of detecting the presence of cancer in a mammal. The method comprises (i) contacting a sample comprising one or more cells from the mammal with any of the inventive TCRs, polypeptides, proteins, nucleic acids, recombinant expression vectors, host cells, populations of cells, or pharmaceutical compositions described herein, thereby forming a complex, and detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, colocrectal cancer, endometrial cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is pancreatic, colorectal, lung, endometrial, ovarian, or prostate cancer. Preferably, the lung cancer is lung adenocarcinoma, the ovarian cancer is epithelial ovarian cancer, and the pancreatic cancer is pancreatic carcinoma. In another preferred embodiment, the cancer is a cancer that expresses the mutated KRAS amino acid sequence with the G12D mutation.

The mammal referred to in the inventive methods can be any mammal. As used herein, the term “mammal” refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

EXAMPLES

The following materials and methods were employed for the experiments described in Examples 1-5.

Patient Samples

Samples were derived from patients enrolled on a clinical protocol (NCT01174121) approved by the institutional-review board (IRB) of the National Cancer Institute (NCI).

Next-Generation Sequencing

For all patients except patient 3971, whole-exomic sequencing (WES) was performed on cryopreserved tumor tissue (embedded in Optimal Cutting Temperature (OCT) medium) and normal peripheral blood cells by Personal Genome Diagnostics (PGDx, Baltimore, Md.) as previously described (Jones et al., *Science,* 330: 228-231 (2010)). PGDx aligned the data to genome build hg18. For patient 3971, whole-genome sequencing (WGS) was performed using the ILLUMINA HISEQ 2000 sequencing system with an average depth of 39.19 for the normal sample and 46.53 for the tumor sample.

The high-performance computational capabilities of the Biowulf Linux cluster at the National Institutes of Health, Bethesda, Md. (biowulf.nih.gov) was also utilized to reanalyze the WES data as described below.

Alignment, Processing and Variant Calling

Alignments were performed using NOVOALIGN MPI from Novocraft (novocraft.com) to human genome build hg19. Duplicates were marked using Picard's MARKDUPLICATES tool. Indel realignment and base recalibration was carried out according to the GATK best practices workflow (broadinstitute.org/gatk). Post cleanup of data, SAMTOOLS MPILEUP software (samtools.sourceforge.net) was used to create pileup files and VARSCAN2 software (varscan.sourceforge.net) was used to call somatic variants. These variants were then annotated using ANNOVAR software (annovar.openbioinformatics.org).

For most WES samples, the data generated by PGDx were reanalyzed and the mutation-call threshold was lowered to generate lower-confidence putative mutations for evaluation using the tandem minigene (TMG) and peptide approach. After the variant calling, the following filters were used to generate putative mutations for evaluation: for patients 3812, 3948, 3995, 4007, and 4032 a cutoff of ≥10% variant frequency and ≥2 variant reads in tumor were used. For patient 4069 a cutoff of ≥8% variant frequency and ≥3 variant reads in the tumor were used. For patients 3978 and 3942, the mutation call threshold was not lowered. For patient 3971 (whole genome sequencing) a cutoff of ≥20% variant frequency in tumor and ≤10% variant frequency in the normal were used to determine the number of mutations and for generation of TMG constructs.

Note, one immunogenic mutation would not have been detected if the mutation call threshold were not lowered (patient 4069, mutation in ZFYVE27). The remaining immunogenic mutations were present in the list of mutations when using previous methods to call mutations referenced above.

Generation of Tumor-Infiltrating Lymphocytes (TIL)

TIL were generated as previously described (Jin et al., *J. Immunother.,* 35: 283-292 (2012)). Briefly, surgically resected tumors were cut into approximately 1-2 mm fragments and placed individually into wells of a 24-well plate containing 2 ml of complete media (CM) containing high dose IL-2 (6000 IU/ml, Chiron, Emeryville, Calif.). CM consisted of Roswell Park Memorial Institute (RPMI) medium supplemented with 10% in-house human serum, 2 mM L-glutamine, 25 mM HEPES and 10 μg/ml gentamicin. In some cases, after the initial outgrowth of TIL (between 2-4 weeks), select cultures were rapidly expanded in gas-permeable G-REX100 flasks using irradiated PBMC at a ratio of 1 to 100 in 400 ml of 50/50 medium, supplemented with 5% human AB serum, 3000 IU/ml of IL-2, and 30 ng/ml of OKT3 antibody (Miltenyi Biotec, Bergisch Gladbach, Germany). 50/50 media consisted of a 1 to 1 mixture of CM with AIM-V media. All cells were cultured at 37° C. with 5% $CO_2$.

For all patients except 3971 and 4069, next-generation sequencing and TIL generation were derived from the same metastatic nodule. For patient 3971, TIL were generated from a lung lesion and whole-genome sequencing was performed on a liver lesion. For patient 4069, TIL were generated from liver lesion and whole-exome sequencing was performed on the primary pancreatic tumor.

Generation of Tandem Minigene (TMG) Constructs and In Vitro Transcribed RNA (IVT) RNA The general description of the tandem minigene (TMG) construct is described in (Lu et al., *Clin. Cancer Res.,* 20: 3401-3410 (2014) and Tran et al., *Science,* 344: 641-645 (2014)). Briefly, for each non-synonymous substitution mutation identified by next-generation sequencing, a "minigene" construct encoding the corresponding amino acid change flanked by 12 amino acids of the wild-type protein sequence was made. Multiple minigenes were strung together to generate a TMG construct. For insertion/deletions (indels), minigenes were made by translating the frame-shifted sequence until the next stop codon. These minigene constructs were codon optimized, synthesized, and cloned (Gene Oracle, Mountain View, Calif.) in-frame using EcoRI and BamHI into a modified pcDNA3.1 vector. This modified vector contains a signal sequence and a DC-LAMP trafficking sequence to enhance processing and presentation, in addition to a poly-A tail to enhance mRNA stability (Bonehill et al., *J. Immunol.,* 172: 6649-6657 (2004)). The nucleotide sequence of all TMGs was verified by standard Sanger sequencing (Gene Oracle). Plasmids encoding the TMGs were linearized with the restriction enzyme NsiI. A control pcDNA3.1/V5-His-TOPO vector encoding green fluorescent protein (GFP) (without the signal sequence and DC-LAMP trafficking sequence) was linearized with NotI. Linearized DNA was precipitated with ethylenediaminetetraacetic acid (EDTA), sodium acetate and ethanol. DNA linearization was verified by standard agarose gel electrophoresis. Approximately 1 μg of linearized plasmid was used for the generation of IVT RNA using the MMESSAGE MMACHINE T7 Ultra kit (Life Technologies, Carlsbad, Calif.) as directed by the manufacturer. RNA was precipitated using the $LiCl_2$ method, and RNA purity and concentrations were assessed using a NANODROP spectrophotometer. RNA was then aliquoted into microtubes and stored at −80° C. until use.

Generation of Autologous Antigen Presenting Cells (APCs)

Monocyte-derived, immature dendritic cells were generated using the plastic adherence method. Briefly, apheresis samples were thawed, washed, set to 5-10×$10^6$ cells/ml with neat AIM-V media (Life Technologies) and then incubated at approximately 1×$10^6$ cells/$cm^2$ in an appropriate sized tissue culture flask and incubated at 37° C., 5% $CO_2$. After 90 minutes (min), non-adherent cells were collected, and the flasks were vigorously washed with AIM-V media, and then incubated with AIM-V media for another 60 min. The flasks were then vigorously washed again with AIM-V media and then the adherent cells were incubated with DC media. DC media included RPMI containing 5% human serum, 100 U/ml penicillin and 100 μg/ml streptomycin, 2 mM L-glutamine, 800 IU/ml granulocyte-macrophage colony-stimulating factor (GM-CSF) (LEUKINE (sargramostim)) and 200 U/ml IL-4 (Peprotech, Rocky Hill, N.J.). On day 2-3, fresh DC media was added to the cultures. Fresh or freeze/thawed DCs were used in experiments on day 4-6 after culture initiation.

Antigen presenting B cells were generated using the CD40L and IL-4 stimulation method. Briefly, human CD19-microbeads (Miltenyi Biotec) were used to positively select B cells from autologous apheresis samples. CD19+ cells were then cultured with irradiated (6000 rad) 3T3 cells stably expressing CD40L (3T3-CD40L) at approximately a 1:1 ratio in B-cell media. B-cell media included Iscove's Modified Dulbecco's Media (IMDM) media (Life Technologies) supplemented with 10% human serum, 100 U/ml penicillin and 100 μg/ml streptomycin, 10 μg/ml gentamicin, 2 mM L-glutamine, and 200 U/ml IL-4 (Peprotech). Fresh B-cell media was added starting on day 3, and media added or replaced every 2-3 days thereafter. Additional irradiated 3T3-CD40L feeder cells were used to re-stimulate B cells every 5-8 days as required. Fresh or freeze/thawed B cells were typically used in experiments 5-8 days after the last stimulation with 3T3-CD40L cells.

RNA Transfections

APCs (DCs or B cells) were harvested, washed 1× with PBS, and then resuspended in OPTI-MEM media (Life Technologies) at 10-30×$10^6$ cells/ml. IVT RNA (4 μg or 8 μg) was aliquoted to the bottom of a 2 mm gap electroporation cuvette, and 50 μl or 100 μl of APCs were added directly to the cuvette. The final RNA concentration used in electroporations was thus 80 μg/ml. Electroporations were carried out using a BTX-830 square wave electroporator. DCs were electroporated with 150 V, 10 ms, and 1 pulse, and B cells were electroporated with 150 V, 20 ms, and 1 pulse. Transfection efficiencies using these settings were routinely between 70-90% as assessed with GFP RNA. All steps were carried out at room temperature. Following electroporation, cells were immediately transferred to polypropylene tubes containing DC- or B-cell media supplemented with the appropriate cytokines. Transfected cells were incubated overnight (12-14 h) at 37° C., 5% $CO_2$. Cells were washed 1× with phosphate-buffered saline (PBS) prior to use in co-culture assays. In co-culture assays, the irrelevant TMG RNA control was a TMG from a different patient.

Peptide Pulsing

DCs or B cells were harvested and then resuspended at 0.5×$10^6$ cells/ml (DCs) or 1×$10^6$ cells/ml (B cells) with either DC or B-cell media containing the appropriate cytokines. Long peptides (usually 25-mers, Genscript, Piscataway, N.J.) were dissolved with dimethyl sulfoxide (DMSO) and pulsed onto the APCs at ~10 μg/ml (or the indicated concentrations for titrations) and incubated overnight at 37° C. with 5% $CO_2$. The following day (usually 12-16 hours (h) after peptide pulsing), APCs were washed 1× prior co-culture with T cells. For short/predicted minimal peptides, APCs were pulsed for ~2 h at 37° C. with ~0.1 to 1 μg/ml peptide (unless otherwise stated), and washed 1× prior to co-culture with T cells.

T-Cell Sorting, Expansion, and Cloning

The BD FACSARIA IIu cell sorter and BD FACSJAZZ cell sorter were used in all experiments requiring cell sorting. In indicated experiments, sorted T cells were expanded using excess irradiated (4000 rad) allogeneic feeder cells (pool of three different donor leukapheresis samples) in 50/50 media containing 30 ng/ml anti-CD3 antibody (OKT3) and 3000 IU/ml IL-2. Cells were typically used in assays 2-3 weeks after the initial stimulation.

In some cases, to study the mutation-reactivity of T cells, CD4 and CD8 T cells from the fresh tumor digest were sorted and expanded based on PD-1 expression since it has been demonstrated that the PD-1$^+$ CD8 T cells in melanoma patients are enriched in tumor-reactive T cells (Gros et al., *J. Clin. Invest.,* 124: 2246-2259 (2014)). Flow-based cell sorting was also used to enrich for mutation-reactive T cells as described below in "Identification and construction of mutation-reactive TCRs."

Co-Culture Assays: IFN-γ ELISPOT, ELISA, and Flow Cytometry for Cell Surface Activation Markers When DCs were used as APCs, approximately 3.5×$10^4$ to 7×$10^4$ DCs were used per well of a 96-well plate. When B cells were used as APCs, approximately 2×$10^5$ cells were used per well of a 96-well plate. In Enzyme-Linked ImmunoSpot (ELISPOT) assays, 1×$10^4$ to 4×$10^4$ effector T cells were used per well. Prior to processing the ELISPOT plates, cells were harvested from the plate and processed for flow cytometry analysis described below. T cells were typically thawed and rested in IL-2 (3000 IU/ml IL-2) containing 50/50 media for at least two days prior to co-culture. All co-cultures were performed in the absence of exogenously added cytokines. For all IFN-γ ELISPOT and flow cytometry assays, plate-bound OKT3 (1 pg/ml) was used as a positive control. For co-cultures with COS-7 and pancreatic cell lines, 1×$10^5$ T cells were co-cultured with 1×$10^5$ target cells overnight. Supernatants were collected and evaluated for IFN-γ using an IFN-γ ELISA.

For IFN-γ ELISPOT assays, briefly, ELISpot PVDF (ELIIP) plates (Millipore, Billerica, Mass. (MAIPSWU) were pre-treated with 50 μl of 70% ethanol per well for 2 min, washed 3× with PBS, and then coated with 50 μl of 10 μg/ml IFN-γ capture antibody (Mabtech, Cincinnati, Ohio) (clone: 1-D1K) and incubated overnight in the fridge. For OKT3 controls, wells were coated with a mixture of IFN-γ capture antibody (10 pg/ml) and OKT3 (1 μg/ml). Prior to co-culture, the plates were washed 3× with PBS, followed by blocking with 50/50 media for at least 1 h at room temperature (RT). After 20-22 h of co-culture, cells were harvested from the ELISPOT plates into a standard 96-well round bottom plate, and then the ELISPOT plates were washed 6× with PBS+0.05% TWEEN-20 detergent (PBS-T), and then incubated for 2 h at RT with 100 μl/well of a 0.22 μm filtered 1 μg/ml biotinylated anti-human IFN-γ detection antibody solution (Mabtech, clone: 7-B6-1). The plate was then washed 3× with PBS-T, followed by a 1 h incubation with 100 μl/well of streptavidin-ALP (Mabtech, diluted 1:3000). The plate was then washed 5× with PBS followed by development with 100 μl/well of 0.45 μm filtered BCIP/NBT substrate solution (KPL, Inc., Gaithersburg, Md.). The reaction was stopped by rinsing thoroughly with cold tap water. ELISPOT plates were scanned and counted using an IMMUNOSPOT plate reader and associated software (Cellular Technologies, Ltd., Shaker Heights, Ohio).

Expression of the T-cell activation markers OX40 and 4-1BB was assessed by flow cytometry at approximately 22-24 h post-stimulation. Briefly, cells that were harvested from the ELISPOT plate were pelleted, washed with Fluorescence Activated Cell Sorting (FACS) buffer (1×PBS supplemented with 1% FBS and 2 mM EDTA), and then stained with the appropriate antibodies for approximately 30 min, at 4° C. in the dark. Cells were washed at least once with FACS buffer prior to acquisition on a BD FACSCANTO II flow cytometer. All data were gated on live (PI negative), single cells. The number of live T-cell events collected usually ranged between 2×$10^3$-8×$10^3$.

Flow Cytometry Antibodies

The following titrated anti-human antibodies were used for cell surface staining: CD3-AF700 (clone: UCHT1), CD4-APC-Cy7 (clone: SK3), CD8-PE-Cy7 (clone: SK), OX40-FITC (clone: Ber-ACT35), and 4-1BB-APC (clone: 4B4-1). All antibodies were from BioLegend (San Diego, Calif.), except CD8-PE-Cy7 and OX40-FITC (BD Bioscience, Franklin Lakes, N.J.). The IO MARK BETA MARK TCR V kit (Beckman Coulter, Schaumburg, Ill.) was used to assess the TCR-Vβ repertoire of indicted T-cell populations. Fluorochrome conjugated anti-mouse TCRβ constant region antibodies (clone: H57-597, eBioscience, San Diego, Calif.) were used to assess TCR-transduction efficiency.

TCR-Vβ Deep Sequencing

TCR-Vβ deep sequencing was performed by IMMUNOSEQ assay, Adaptive Biotechnologies (Seattle, Wash.) on genomic DNA isolated from peripheral blood, T cells, and frozen tumor tissue using the DNEASY blood and tissue kit (Qiagen, Venlo, Netherlands). Only productive TCR rearrangements were used in the calculations of TCR frequencies.

Identification and Construction of Mutation-Reactive TCRs

Several methods were used to identify mutation-reactive TCR sequences. First, T cells that upregulated an activation marker (4-1BB or OX40) upon co-culture with mutated TMGs or peptides were FACS purified and then directly sequenced or further expanded as described below. Second, in cases where there was a dominant reactivity that correlated with a dominant TCR-Vβ clonotype (as determined using the IO MARK BETA MARK TCR V kit), the dominant TCR-Vβ expressing T cells were FACS purified and then either directly sequenced or further expanded before sequencing.

In most cases, after expansion, the enriched mutation-reactive cells were pelleted and total RNA isolated (RNEASY Mini kit, Qiagen). Total RNA then underwent 5' RACE as directed by manufacturer (SMARTer RACE cDNA amplification kit, Clontech, Mountain View, Calif.) using TCR-alpha and -beta chain constant primers. Program 1 of the kit was used for the PCR, with a modification to the extension time (2 min instead of 3 min). The sequences of the alpha and beta chain constant primers are: TCR-alpha, SEQ ID NO: 21; TCR-beta, SEQ ID NO: 22. TCR PCR products were then isolated by standard agarose gel electrophoresis and gel extraction (Clontech). Products were then either directly sequenced or TOPO-TA cloned followed by sequencing of individual colonies (Macrogen, Seoul, Korea). In other cases, TCR-Vβ deep sequencing was performed on the enriched mutation-reactive cells (Adaptive Biotechnologies, Seattle, Wash.), which often yielded a highly dominant TCR-Vβ sequence. Co-culture assays using the enriched mutation-reactive T-cell populations and/or TCR-transduced T cells were performed to verify that the populations were in fact reactive against the identified mutation.

Construction of the mutation-reactive TCRs was done by fusing the TCR-alpha V-J regions to the mouse TCR-alpha constant chain, and the TCR-beta-V-D-J regions to the mouse TCR-beta constant chains. The mouse TCR-alpha constant chain had the amino acid sequence of SEQ ID NO: 24, and the mouse TCR-beta constant chain had the amino acid sequence of SEQ ID NO: 25. The alpha and beta chains were separated by a furin SGSG P2A linker (SEQ ID NO: 23). Use of mouse TCR constant regions promotes pairing of the introduced TCR and also facilitates identification of positively transduced T cells by flow cytometry using an antibody specific for the mouse TCR-f chain (eBioscience). In cases there were two putative TCR alpha chains paired with one beta chain, both TCRs were constructed and evaluated for reactivity. TCR constructs were synthesized and cloned into the MSGV1 retroviral vector (Gene Oracle).

Cell Line Transfection and Transduction

COS-7 cells were transfected with KRAS wild-type or G12D cDNA (200 ng each) in combination with one of the HLA-B and -C allele cDNAs (50 ng each) from patient 3995 (Table 1). Only the HLA-B and HLA-C alleles were tested because preliminary experiments ruled out HLA-A as the restriction element for KRAS G12D reactivity. Transfections were performed in a 96-well plate. The human pancreatic cancer cell lines ASPC-1, MDA-Panc48, PK-45p, FA6-2, and HPAC-1, which all express KRASG12D, in addition to the KRASG12D-negative cell lines BxPC-3 (KRAS wt), A818.8 (KRASG12R), SK-PC3 (KRASG12V), and MIA PaCa-2 (KRASG12C) were transduced with nothing or retrovirus encoding HLA-Cw*08:02.

TABLE 1

| | HLA-I | | | | | |
|---|---|---|---|---|---|---|
| Patient ID | A | A | B | B | C | C |
| 3995 | 30:02 | 32:01 | 14:01 | 18:01 | 05:01 | 08:02 |

TCR Transduction of Peripheral Blood T Cells

Autologous apheresis samples were thawed and set to $2\times10^6$ cells/ml in T-cell media, which consists of a 50/50 mixture of RPMI and AIM-V media supplemented with 5% in-house human serum, 10 μg/ml gentamicin, 100 U/ml penicillin and 100 μg/ml streptomycin, 1.25 μg/ml FUNGIZONE amphotericin B and 2 mM L-glutamine. $2\times10^6$ cells (1 ml) were stimulated in a 24-well plate with 50 ng/ml soluble OKT3 (Miltenyi Biotec) and 300 IU/ml rhu IL-2 (Chiron) for 2 days prior to retroviral transduction. To generate transient retroviral supernatants, the retroviral vector MSGV1 encoding the mutation-reactive TCRs (1.5 μg/well) and the envelope encoding plasmid RD114 (0.75 μg/well) were co-transfected into the retroviral packaging cell line 293GP ($1\times10^6$ cells per well of a 6-well poly-D-lysine-coated plates, plated the day prior to transfection) using LIPOFECTAMINE 2000 reagent (Life Technologies). Retroviral supernatants were collected at 42-48 h after transfection, diluted 1:1 with DMEM media, and then centrifuged onto RETRONECTIN reagent-coated (10 μg/ml, Takara, Shiga, Japan), non-tissue culture-treated 6-well plates at 2,000 g for 2 h at 32° C. Activated T cells ($2\times10^6$ per well, at $0.5\times10^6$ cells/ml in IL-2 containing T-cell media) were then spun onto the retrovirus plates for 10 min at 300 g. Activated T cells were transduced overnight, removed from the plates and further cultured in IL-2 containing T-cell media. GFP and mock transduction controls were included in transduction experiments. Cells were typically assayed 10-14 days post-retroviral transduction.

Example 1

This example demonstrates the identification of somatic mutations present in metastatic tumors.

Whole-exome or whole-genome sequencing was used to identify somatic mutations present in metastatic tumors derived from 9 patients with cancers originating from the colon, rectum, esophagus, bile ducts, or pancreas (Table 2). The number of mutations ranged from 10 to 155 when using previous methods to call mutations (Table 2) (Tran et al., *Science,* 344: 641-645 (2014)). However, to evaluate any low coverage and low confidence mutations, the mutation call criteria were relaxed for most samples and thus between 38-264 putative mutations were evaluated (Table 2).

TABLE 2

| Patient ID | Age/sex | Tumor type | # of mutations** | # of mutations assessed*** | # TIL cultures assessed | # TIL cultures with mutation reactivity† | Mutated gene recognized | Amino acid change | T cell type | Frequency of mutation-reactive TCR in tumor (%) | Rank of mutat.-reactive TCR in tumor |
|---|---|---|---|---|---|---|---|---|---|---|---|
| 3737* | 45/F | Bile duct | 26 | 25 | 5 | 5 | ERBB2IP | E805G | CD4 | 0.009 | 2718 |
| | | | | | | | | E805G | CD4 | 0.375 | 10 |
| 3812 | 44/M | Bile duct | 48 | 179 | 5 | 0 | — | — | — | — | — |
| 3942 | 46/F | Rectal | 155 | 144 | 6 | 2 | NUP98 | A359D | CD8 | 0.67 | 5 |
| | | | | | | 4 | KARS | D356H | CD8 | 0.020 | 1143 |
| | | | | | | 3 | GPD2 | E426K | CD4 | 0.037 | 862 |
| 3948 | 48/M | Esophageal | 84 | 211 | 5 | 2 | PLEC | E1179K | CD4 | NE | NE |
| | | | | | | 2 | XPO7 | P274S | CD4 | NE | NE |
| | | | | | | 2 | AKAP2 | Q418K | CD4 | NE | NE |
| 3971 | 49/M | Colon | 118 | 118 | 23 | 11 | CASP8 | F67V | CD8 | 1.25 | 3 |
| 3978 | 46/F | Bile duct | 39 | 38 | 9‡ | 1§ | ITGB4 | S1002I | CD4 | NE | NE |
| 3995 | 50/M | Colon | 58 | 154 | 19‡ | 2 | TUBGCP2 | P293L | CD8 | 0.023 | 1056 |
| | | | | | | 15 | RNF213 | N1702S | CD8 | 0.60 | 15 |
| | | | | | | 2 | KRAS | G12D | CD8 | 0.055 | 527 |
| 4007 | 52/M | Colon | 134 | 264 | 25‡ | 4 | SKIV2L | R653H | CD8 | 0.090 | 121 |
| | | | | | | | | R653H | CD8 | 0.014 | 887 |
| | | | | | | 5 | H3F3B | A48T | CD8 | 1.19 | 4 |
| | | | | | | 1§ | KLHDC7A | E527K | CD4 | NE | NE |
| | | | | | | 1§ | MUC4 | S3707T H3709Q T3710A | CD4 | NE | NE |
| 4032 | 46/M | Colon | 101 | 222 | 24 | 12 | API5 | R243Q | CD8 | 0.083 | 126 |
| | | | | | | | | R243Q | CD8 | 0.059 | 187 |
| | | | | | | 1 | RNF10 | E572K | CD8 | 0.030 | 423 |
| | | | | | | 7 | PHLPP1 | G566E | CD8 | 0.081 | 129 |
| 4069 | 57/M | Pancreatic | 10 | 97 | 15 | 1 | ZFYVE27 | R6H | CD8 | 0.088 | 278 |

*Patient 3737 previously reported in Tran et al., Science, 344: 641-645 (2014).
**As determined by Personal Genome Diagnostics (PGDx) from whole-exome sequencing.
***As determined when mutation call criteria was relaxed. The mutation call criteria was not relaxed for patients 3737, 3942 and 3978.
†Reactivity as determined by IFN-γ ELISPOT or flow cytometry for 4-1BB or OX40 upregulation upon co-culture with mutated TMGs or peptides.
‡The indicated number of TIL cultures includes T-cell populations that were sorted and expanded from a tumor digest based on PD-1 expression.
§Identified from a FACS purified TIL population.
NE = not evaluated.

Example 2

This example demonstrates the isolation of T cells that recognize KRAS G12D from a patient with colorectal cancer (Patient No. 3995).

Multiple TIL cultures were generated from the metastatic lesions of each patient shown in Table 2. To test whether any of the TIL cultures from each patient recognized their own tumor mutations, a tandem minigene (TMG) approach was used as previously described (Lu et al., *Clin. Cancer Res.,* 20: 3401-3410 (2014); Tran et al., *Science,* 344: 641-645 (2014)). Briefly, these TMGs are comprised of a string of minigenes which are genetic constructs that encode an identified mutation flanked on each side by the 12 wild-type amino acids from the parent protein, except in the case of frameshift mutations where the cDNA was translated until the next stop codon. After in vitro transcription, the TMG RNAs were then individually transfected into autologous antigen presenting cells (APCs), allowing for the potential processing and presentation of all mutated epitopes by each of the patient's MHC class I and class II molecules, followed by a co-culture with the different TIL cultures.

For Patient 3995, 19 different TIL cultures were co-cultured with autologous DCs transfected with an irrelevant tandem minigene (TMG) RNA, or one of 10 different TMG constructs (TMG-1 to TMG-10) which together encoded 154 minigenes that were identified by whole-exomic sequencing as described in Example 1.

TIL cultures were identified that were reactive against TMG-2 and TMG-5, as determined by IFN-γ ELISPOT. To identify which mutated antigens were being recognized in TMG-2 and TMG-5, the TMG-2 and TMG-5 reactive cells were co-cultured with autologous DCs that were individually pulsed with the mutated peptides encoded by TMG-2 or TMG-5, respectively. Patient-unique mutation-specific CD8+ T cells against RNF213$^{N1702S}$ and TUBGCP2$^{P293L}$ were identified.

In addition, a low level CD8+ TIL reactivity against the KRAS$^{G12D}$ hotspot mutation was observed. This TIL culture was reactive against TMG-3, as determined by IFN-γ ELISPOT. TMG-3 encoded for 13 mutated minigenes including the KRAS G12D hotspot mutation. The TMG-3 reactive cells were co-cultured with autologous DCs that were pulsed with wild-type (wt) (SEQ ID NO: 19) or mutated KRAS G12D long (SEQ ID NO: 20) (24-mer) peptides. The number of spots counted per $3\times10^4$ TILs was 0 for the TIL co-cultured with wt KRAS peptide and 59 for the TIL co-cultured with the mutated KRAS G12D peptide. Accordingly, KRAS G12D was identified as the mutation recognized by the TMG-3-reactive TIL. Notably, the mutated KRAS long peptide SEQ ID NO: 20 recognized by the cells encompassed the minimal T-cell epitope GADGVGKSAL (SEQ ID NO: 18) that is predicted to rank among the top 2% of peptides that bound to the MHC-I molecule C08:02 expressed by the patient.

The CD8+ T cells that upregulated 4-1BB upon KRAS G12D stimulation were FACS purified and expanded. IFN-γ ELISPOT assay and flow cytometric analysis of 4-1BB expression was carried out with respect to the KRAS G12D enriched CD8+ T cells that were co-cultured overnight with DCs pulsed with wt or KRAS G12D long peptide, or DCs transfected with full-length wt or KRAS G12D RNA.

It was confirmed by IFN-γ ELISPOT assay and flow cytometric analysis of 4-1BB expression that the enriched population (i) specifically recognized APCs when pulsed with the mutated $KRAS^{G12D}$ peptide or transfected with full-length $KRAS^{G12D}$ RNA and (ii) did not specifically recognize APCs when pulsed with the WT KRAS peptide or transfected with full-length WT KRAS RNA.

The enriched population of $KRAS^{G12D}$-reactive TILs were cocultured for 6 hours with pancreatic cancer cell line MDA-Panc48 ($KRAS^{G12D}$), HPAC ($KRAS^{G12D}$), or MIA PaCa-2 ($KRAS^{G12C}$) transduced with nothing (Mock) or the HLA-C*08:02 allele. Flow cytometry was used to assess CD107a expression and TNF production by intracellular cytokine staining. Autologous APCs (peripheral blood mononuclear cells) pulsed overnight with wt or $KRAS^{G12D}$ 24-AA-long peptides were used as control target cells. Data were gated on CD8+ T cells expressing the $KRAS^{G12D}$-reactive TCR Vβ5.2.

The results showed that the KRAS-mutation reactive TILs specifically produced tumor necrosis factor (TNF) and displayed cytolytic potential against pancreatic cancer cell lines expressing HLAC*08:02 and $KRAS^{G12D}$.

Example 3

This example demonstrates the isolation of an anti-KRAS G12D TCR from the $KRAS^{G12D}$-specific T cells of Example 2. This example also demonstrates that autologous open-repertoire T cells genetically engineered with the isolated TCR provided HLA-Cw*08:02-restricted recognition of COS-7 cells transfected with $KRAS^{G12D}$.

The nucleotide sequences encoding the alpha and beta chain variable regions of the TCR of the KRAS G12D-reactive cells isolated in Example 2 were isolated from the T cells. A nucleotide sequence encoding the alpha chain variable region (SEQ ID NO: 9) and beta chain variable region (SEQ ID NO: 10) fused to mouse TCR alpha constant chain (SEQ ID NO: 24) and mouse beta constant chain (SEQ ID NO: 25), respectively, were cloned into an expression vector. Autologous open-repertoire T cells were genetically engineered to express the anti-KRAS G12D TCR.

The genetically engineered cells were co-cultured with COS-7 cells that were co-transfected with (i) nothing or a nucleotide sequence encoding WT KRAS or KRAS G12D along with (ii) no HLA molecule or the individual HLA-B and -C alleles expressed by the patient (B*14:01, B*18:01, Cw*05:01, or Cw*08:02). IFN-γ secretion was measured by IFN-γ ELISA assay. The results showed that T cells genetically engineered with the TCR isolated from the $KRAS^{G12D}$-specific T cells redirected HLA-Cw*08:02-restricted reactivity to COS-7 cells transfected with $KRAS^{G12D}$. The results also showed that the genetically engineered T cells did not recognize any of the COS-7 cells that were transfected with WT KRAS, no KRAS, or no HLA molecule. The genetically engineered T cells also did not recognize the COS-7 cells that were co-transfected with both (i) KRAS G12D and (ii) the B*14:01, B*18:01, or Cw*05:01 molecule.

Example 4

This example demonstrates that autologous open-repertoire T cells genetically engineered with the TCR isolated in Example 3 provided HLA-Cw*08:02-restricted recognition of $KRAS^{G12D}$ expressing pancreatic cancer cell lines.

Autologous open-repertoire T cells were genetically engineered to express the anti-KRAS G12D TCR of Example 3. The genetically engineered T cells were co-cultured with various pancreatic cancer cell lines transduced with nothing (Mock) or the HLA-Cw*08:02 allele. The pancreatic cell lines were as follows: ASPC-1 (KRAS G12D+); MDA-Panc48 (KRAS G12D+); PK-45p (KRAS G12D+); FA6-2 (KRAS G12D+); HPAC (KRAS G12D+); BxPC-3 (KRAS wt); A818.8 ($KRAS^{G12R}$); SK-PC3 ($KRAS^{G12V}$); and MIA PaCa-2 ($KRAS^{G12C}$). IFN-γ secretion was measured by ELISA.

The results showed that genetic engineering of autologous open-repertoire T cells with the TCR isolated from the $KRAS^{G12D}$-specific T cells redirected HLA-Cw*08:02-restricted reactivity to $KRAS^{G12D}$ expressing pancreatic cancer cell lines. The results also showed that the genetically engineered cells did not recognize the BxPC-3 (KRAS wt); A818.8 ($KRAS^{G12R}$); SK-PC3 ($KRAS^{G12V}$); or MIA PaCa-2 ($KRAS^{G12C}$) cell lines. No recognition of pancreatic cell lines was observed in the absence of HLA-Cw*08:02.

Example 5

This example demonstrates the frequency of the mutation-reactive T cells infiltrating the metastatic lesions of the patients shown in Table 2.

To determine the endogenous frequency of the mutation-reactive T cells infiltrating the metastatic lesions, TCR-Vβ deep sequencing was performed on the cryopreserved metastatic tumor lesions. As shown in Table 2, the frequency of the identified mutation-reactive T cells infiltrating the metastatic lesions was variable, ranging from 0.009-1.25% of all T cells within a given tumor. Of the 17 identified mutation-reactive TCRs, 4 ranked within the top 10 most frequent TCRs within the tumor (rank range: 3-2718, Table 2). Of note, often only a minority of TIL cultures derived from the same metastatic lesion harbored detectable levels of IFN-γ producing mutation-reactive T cells, and furthermore, different TIL cultures were enriched for T cells reactive to different mutations (Table 2). Without being bound to a particular theory or mechanism, this heterogeneity in neo-epitope T-cell reactivity may be a function of the intratumoral genomic heterogeneity observed in human cancers.

Example 6

This example demonstrates that T cells transduced with a nucleotide sequence encoding the anti-mutated KRAS TCR of Example 3 recognized autologous dendritic cells pulsed with mutated KRAS peptides.

T cells were transduced with a nucleotide sequence encoding the anti-mutated KRAS TCR of Example 3. The transduced cells were co-cultured with autologous dendritic cells pulsed with one of the peptides shown in Table 3 at various concentrations. IFN-γ was measured by ELISA. The results are shown in FIG. 1.

TABLE 3

| Mutated KRAS peptides | | WT KRAS peptides | |
|---|---|---|---|
| Mutated $KRAS_{10-18}$ | GA**D**GVGKSA (SEQ ID NO: 18) | WT $KRAS_{10-18}$ | GA**G**GVGKSA (SEQ ID NO: 17) |

TABLE 3 -continued

| Mutated KRAS peptides | | WT KRAS peptides | |
|---|---|---|---|
| Mutated $KRAS_{9-18}$ | VGADGVGKSA (SEQ ID NO: 31) | WT $KRAS_{9-18}$ | VGAGGVGKSA (SEQ ID NO: 32) |
| Mutated $KRAS_{10-19}$ | GADGVGKSAL (SEQ ID NO: 30) | WT $KRAS_{10-19}$ | GAGGVGKSAL (SEQ ID NO: 33) |

As shown in FIG. 1, T cells transduced with a nucleotide sequence encoding with the anti-mutated KRAS TCR of Example 3 recognized each of the mutated KRAS peptides and did not recognize any of the WT KRAS peptides.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified TCR comprising:

(I) an α chain complementarity determining region (CDR) 1 comprising the amino acid sequence of SEQ ID NO: 3, an α chain CDR2 comprising the amino acid sequence of SEQ ID NO: 4, and an α chain CDR3 comprising the amino acid sequence of SEQ ID NO: 5; and (II) a β chain CDR1 comprising the amino acid sequence of SEQ ID NO: 6, a β chain CDR2 comprising the amino acid sequence of SEQ ID NO: 7, and a β chain CDR3 comprising the amino acid sequence of SEQ ID NO: 8.

2. The isolated or purified TCR of claim 1, comprising:

(I) an α chain variable region comprising the amino acid sequence of SEQ ID NO: 9;

(II) a β chain variable region comprising the amino acid sequence of SEQ ID NO: 10; or (III) both (I) and (II).

3. The isolated or purified TCR of claim 1, further comprising:

(a) an α chain constant region comprising the amino acid sequence of SEQ ID NO: 11, wherein:

(i) X at position 48 of SEQ ID NO: 11 is Thr or Cys;

(ii) X at position 112 of SEQ ID NO: 11 is Ser, Ala, Val, Leu, Ile, Pro, Phe, Met, or Trp;

(iii) X at position 114 of SEQ ID NO: 11 is Met, Ala, Val, Leu, Ile, Pro, Phe, or Trp; and (iv) X at position 115 of SEQ ID NO: 11 is Gly, Ala, Val, Leu, Ile, Pro, Phe, Met, or Trp;

(b) a β chain constant region comprising the amino acid sequence of SEQ ID NO: 12, wherein X at position 57 of SEQ ID NO: 12 is Ser or Cys; or (c) both (a) and (b).

4. The isolated or purified TCR of claim 1, comprising:

(a) an α chain comprising the amino acid sequence of SEQ ID NO: 13, wherein:

(i) X at position 177 of SEQ ID NO: 13 is Thr or Cys;
(ii) X at position 241 of SEQ ID NO: 13 is Ser, Ala, Val, Leu, Ile, Pro, Phe, Met, or Trp;
(iii) X at position 243 of SEQ ID NO: 13 is Met, Ala, Val, Leu, Ile, Pro, Phe, or Trp; and
(iv) X at position 244 of SEQ ID NO: 13 is Gly, Ala, Val, Leu, Ile, Pro, Phe, Met, or Trp;
(b) a β chain comprising the amino acid sequence of SEQ ID NO: 14, wherein X at position 189 of SEQ ID NO: 14 is Ser or Cys; or
(c) both (a) and (b).

5. An isolated or purified polypeptide comprising a functional portion of the TCR of claim 1, wherein the functional portion comprises the amino acid sequences of SEQ ID NOs: 3-8.

6. The isolated or purified polypeptide of claim 5, wherein the functional portion comprises the amino acid sequences of (I) SEQ ID NO: 9; (II) SEQ ID NO: 10; or (III) SEQ ID NOs: 9-10.

7. The isolated or purified polypeptide of claim 5, further comprising:
(a) the amino acid sequence of SEQ ID NO: 11, wherein:
(i) X at position 48 of SEQ ID NO: 11 is Thr or Cys;
(ii) X at position 112 of SEQ ID NO: 11 is Ser, Ala, Val, Leu, Ile, Pro, Phe, Met, or Trp;
(iii) X at position 114 of SEQ ID NO: 11 is Met, Ala, Val, Leu, Ile, Pro, Phe, or Trp;
and
(iv) X at position 115 of SEQ ID NO: 11 is Gly, Ala, Val, Leu, Ile, Pro, Phe, Met, or Trp;
(b) the amino acid sequence of SEQ ID NO: 12, wherein X at position 57 of SEQ ID NO: 12 is Ser or Cys; or
(c) both (a) and (b).

8. The isolated or purified polypeptide of claim 5, comprising:
(a) the amino acid sequence of SEQ ID NO: 13, wherein:
(i) X at position 177 of SEQ ID NO: 13 is Thr or Cys;
(ii) X at position 241 of SEQ ID NO: 13 is Ser, Ala, Val, Leu, Ile, Pro, Phe, Met, or Trp;
(iii) X at position 243 of SEQ ID NO: 13 is Met, Ala, Val, Leu, Ile, Pro, Phe, or Trp; and
(iv) X at position 244 of SEQ ID NO: 13 is Gly, Ala, Val, Leu, Ile, Pro, Phe, Met, or Trp;
(b) the amino acid sequence of SEQ ID NO: 14, wherein X at position 189 of SEQ ID NO: 14 is Ser or Cys; or
(c) both (a) and (b).

9. An isolated or purified protein comprising a functional portion of the TCR of claim 1, wherein the functional portion comprises the amino acid sequences of SEQ ID NOs: 3-8, and wherein the protein comprises (I) a first polypeptide chain comprising the amino acid sequences of SEQ ID NOs: 3-5 and (II) a second polypeptide chain comprising the amino acid sequences of SEQ ID NOs: 6-8.

10. The isolated or purified protein of claim 9, comprising (I) a first polypeptide chain comprising the amino acid sequence of SEQ ID NO: 9; (II) a second polypeptide chain comprising the amino acid sequence of SEQ ID NO: 10; or (III) both (I) and (II).

11. The isolated or purified protein of claim 9, comprising:
(a) a first polypeptide chain comprising the amino acid sequence of SEQ ID NO: 11, wherein:
(i) X at position 48 of SEQ ID NO: 11 is Thr or Cys;
(ii) X at position 112 of SEQ ID NO: 11 is Ser, Ala, Val, Leu, Ile, Pro, Phe, Met, or Trp;
(iii) X at position 114 of SEQ ID NO: 11 is Met, Ala, Val, Leu, Ile, Pro, Phe, or Trp; and
(iv) X at position 115 of SEQ ID NO: 11 is Gly, Ala, Val, Leu, Ile, Pro, Phe, Met, or Trp;
(b) a second polypeptide chain comprising the amino acid sequence of SEQ ID NO: 12, wherein X at position 57 of SEQ ID NO: 12 is Ser or Cys; or
(c) both (a) and (b).

12. The isolated or purified protein of claim 9, comprising:
(a) a first polypeptide chain comprising the amino acid sequence of SEQ ID NO: 13, wherein:
(i) X at position 177 of SEQ ID NO: 13 is Thr or Cys;
(ii) X at position 241 of SEQ ID NO: 13 is Ser, Ala, Val, Leu, Ile, Pro, Phe, Met, or Trp;
(iii) X at position 243 of SEQ ID NO: 13 is Met, Ala, Val, Leu, Ile, Pro, Phe, or Trp; and
(iv) X at position 244 of SEQ ID NO: 13 is Gly, Ala, Val, Leu, Ile, Pro, Phe, Met, or Trp;
(b) a second polypeptide chain comprising the amino acid sequence of SEQ ID NO: 14, wherein X at position 189 of SEQ ID NO: 14 is Ser or Cys; or
(c) both (a) and (b).

13. An isolated or purified nucleic acid comprising a nucleotide sequence encoding the TCR of claim 1.

14. A recombinant expression vector comprising the nucleic acid of claim 13.

15. An isolated or purified host cell comprising the recombinant expression vector of claim 14.

16. A population of cells comprising at least two isolated or purified host cells of claim 15.

17. A pharmaceutical composition comprising the TCR of claim 1 and a pharmaceutically acceptable carrier.

18. A method of detecting the presence of an (HLA)-Cw8 and KRAS G12D expressing cancer in a mammal, the method comprising:
(a) contacting a sample comprising cells of the cancer with the TCR of claim 1, thereby forming a TCR-cancer cell complex; and
(b) detecting the TCR-cancer cell complex.

19. A method of treating or preventing an (HLA)-Cw8 and KRAS G12D expressing cancer in a mammal, the method comprising administering to the mammal the TCR of claim 1 in an amount effective to treat or prevent the (HLA)-Cw8 and KRAS G12D expressing cancer in the mammal.

20. The method of claim 19, wherein the cancer is pancreatic, colorectal, lung, endometrial, ovarian, or prostate cancer.

* * * * *

SEQUENCE LISTING

```
<160> NUMBER OF SEQ ID NOS: 33

<210> SEQ ID NO 1
<211> LENGTH: 189
<212> TYPE: PRT
<213> ORGANISM: Homo sapiens

<400> SEQUENCE: 1

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160
```

```
Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185


<210> SEQ ID NO 2
<211> LENGTH: 188
<212> TYPE: PRT
<213> ORGANISM: Homo sapiens

<400> SEQUENCE: 2

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185


<210> SEQ ID NO 3
<211> LENGTH: 7
<212> TYPE: PRT
<213> ORGANISM: Homo sapiens

<400> SEQUENCE: 3

Asn Ile Ala Thr Asn Asp Tyr
1               5


<210> SEQ ID NO 4
<211> LENGTH: 5
<212> TYPE: PRT
<213> ORGANISM: Homo sapiens

<400> SEQUENCE: 4

Gly Tyr Lys Thr Lys
1               5


<210> SEQ ID NO 5
<211> LENGTH: 13
<212> TYPE: PRT
<213> ORGANISM: Homo sapiens
```

<400> SEQUENCE: 5

```
Leu Val Gly Asp Met Asp Gln Ala Gly Thr Ala Leu Ile
1               5                   10
```

<210> SEQ ID NO 6
<211> LENGTH: 5
<212> TYPE: PRT
<213> ORGANISM: Homo sapiens

<400> SEQUENCE: 6

```
Ser Gly His Asp Thr
1               5
```

<210> SEQ ID NO 7
<211> LENGTH: 6
<212> TYPE: PRT
<213> ORGANISM: Homo sapiens

<400> SEQUENCE: 7

```
Tyr Tyr Glu Glu Glu Glu
1               5
```

<210> SEQ ID NO 8
<211> LENGTH: 12
<212> TYPE: PRT
<213> ORGANISM: Homo sapiens

<400> SEQUENCE: 8

```
Ala Ser Ser Leu Gly Gln Thr Asn Tyr Gly Tyr Thr
1               5                   10
```

<210> SEQ ID NO 9
<211> LENGTH: 129
<212> TYPE: PRT
<213> ORGANISM: Homo sapiens

<400> SEQUENCE: 9

```
Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Asp Met Asp Gln
            100                 105                 110

Ala Gly Thr Ala Leu Ile Phe Gly Lys Gly Thr Thr Leu Ser Val Ser
        115                 120                 125

Ser
```

<210> SEQ ID NO 10
<211> LENGTH: 132
<212> TYPE: PRT
<213> ORGANISM: Homo sapiens

<400> SEQUENCE: 10

```
Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Gly Gln Thr Asn Tyr Gly Tyr Thr Phe Gly Ser Gly Thr Arg
        115                 120                 125

Leu Thr Val Val
    130


<210> SEQ ID NO 11
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (48)..(48)
<223> OTHER INFORMATION: X at position 48 is Thr or Cys
<220> FEATURE:
<221> NAME/KEY: MISC_FEATURE
<222> LOCATION: (112)..(112)
<223> OTHER INFORMATION: X at position 112 is Ser, Ala, Val, Leu, Ile,
      Pro, Phe, Met, or Trp
<220> FEATURE:
<221> NAME/KEY: MISC_FEATURE
<222> LOCATION: (114)..(114)
<223> OTHER INFORMATION: X at position 114 is Met, Ala, Val, Leu, Ile,
      Pro, Phe, or Trp
<220> FEATURE:
<221> NAME/KEY: MISC_FEATURE
<222> LOCATION: (115)..(115)
<223> OTHER INFORMATION: X at position 115 is Gly, Ala, Val, Leu, Ile,
      Pro, Phe, Met, or Trp

<400> SEQUENCE: 11

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Xaa
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Xaa
            100                 105                 110

Val Xaa Xaa Leu Arg Ile Leu Leu Leu Lys Val Ala Gly Phe Asn Leu
```

-continued

```
        115                 120                 125

Leu Met Thr Leu Arg Leu Trp Ser Ser
    130                 135


<210> SEQ ID NO 12
<211> LENGTH: 173
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (57)..(57)
<223> OTHER INFORMATION: X at position 57 is Ser or Cys

<400> SEQUENCE: 12

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Xaa Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170


<210> SEQ ID NO 13
<211> LENGTH: 266
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (177)..(177)
<223> OTHER INFORMATION: X at position 177 is Thr or Cys
<220> FEATURE:
<221> NAME/KEY: MISC_FEATURE
<222> LOCATION: (241)..(241)
<223> OTHER INFORMATION: X at position 241 is Ser, Ala, Val, Leu, Ile,
      Pro, Phe, Met, or Trp
<220> FEATURE:
<221> NAME/KEY: MISC_FEATURE
<222> LOCATION: (243)..(243)
<223> OTHER INFORMATION: X at position 243 is Met, Ala, Val, Leu, Ile,
      Pro, Phe, or Trp
<220> FEATURE:
<221> NAME/KEY: MISC_FEATURE
<222> LOCATION: (244)..(244)
<223> OTHER INFORMATION: X at position 244 is Gly, Ala, Val, Leu, Ile,
      Pro, Phe, Met, or Trp
```

-continued

<400> SEQUENCE: 13

```
Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Asp Met Asp Gln
            100                 105                 110

Ala Gly Thr Ala Leu Ile Phe Gly Lys Gly Thr Thr Leu Ser Val Ser
        115                 120                 125

Ser Asp Ile Gln Asn Pro Glu Pro Ala Val Tyr Gln Leu Lys Asp Pro
    130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Xaa Val Leu Asp Met Lys Ala Met Asp Ser Lys Ser Asn Gly Ala Ile
            180                 185                 190

Ala Trp Ser Asn Gln Thr Ser Phe Thr Cys Gln Asp Ile Phe Lys Glu
        195                 200                 205

Thr Asn Ala Thr Tyr Pro Ser Ser Asp Val Pro Cys Asp Ala Thr Leu
    210                 215                 220

Thr Glu Lys Ser Phe Glu Thr Asp Met Asn Leu Asn Phe Gln Asn Leu
225                 230                 235                 240

Xaa Val Xaa Xaa Leu Arg Ile Leu Leu Leu Lys Val Ala Gly Phe Asn
                245                 250                 255

Leu Leu Met Thr Leu Arg Leu Trp Ser Ser
            260                 265
```

<210> SEQ ID NO 14
<211> LENGTH: 305
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (189)..(189)
<223> OTHER INFORMATION: X at position 189 is Ser or Cys

<400> SEQUENCE: 14

```
Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60
```

Ile Phe Gln Tyr Tyr Glu Glu Glu Glu Arg Gln Arg Gly Asn Phe Pro
65 70 75 80

Asp Arg Phe Ser Gly His Gln Phe Pro Asn Tyr Ser Ser Glu Leu Asn
85 90 95

Val Asn Ala Leu Leu Leu Gly Asp Ser Ala Leu Tyr Leu Cys Ala Ser
100 105 110

Ser Leu Gly Gln Thr Asn Tyr Gly Tyr Thr Phe Gly Ser Gly Thr Arg
115 120 125

Leu Thr Val Val Glu Asp Leu Arg Asn Val Thr Pro Pro Lys Val Ser
130 135 140

Leu Phe Glu Pro Ser Lys Ala Glu Ile Ala Asn Lys Gln Lys Ala Thr
145 150 155 160

Leu Val Cys Leu Ala Arg Gly Phe Phe Pro Asp His Val Glu Leu Ser
165 170 175

Trp Trp Val Asn Gly Lys Glu Val His Ser Gly Val Xaa Thr Asp Pro
180 185 190

Gln Ala Tyr Lys Glu Ser Asn Tyr Ser Tyr Cys Leu Ser Ser Arg Leu
195 200 205

Arg Val Ser Ala Thr Phe Trp His Asn Pro Arg Asn His Phe Arg Cys
210 215 220

Gln Val Gln Phe His Gly Leu Ser Glu Glu Asp Lys Trp Pro Glu Gly
225 230 235 240

Ser Pro Lys Pro Val Thr Gln Asn Ile Ser Ala Glu Ala Trp Gly Arg
245 250 255

Ala Asp Cys Gly Ile Thr Ser Ala Ser Tyr Gln Gln Gly Val Leu Ser
260 265 270

Ala Thr Ile Leu Tyr Glu Ile Leu Leu Gly Lys Ala Thr Leu Tyr Ala
275 280 285

Val Leu Val Ser Thr Leu Val Val Met Ala Met Val Lys Arg Lys Asn
290 295 300

Ser
305

<210> SEQ ID NO 15
<211> LENGTH: 189
<212> TYPE: PRT
<213> ORGANISM: Homo sapiens

<400> SEQUENCE: 15

Met Thr Glu Tyr Lys Leu Val Val Val Gly Ala Asp Gly Val Gly Lys
1 5 10 15

Ser Ala Leu Thr Ile Gln Leu Ile Gln Asn His Phe Val Asp Glu Tyr
20 25 30

Asp Pro Thr Ile Glu Asp Ser Tyr Arg Lys Gln Val Val Ile Asp Gly
35 40 45

Glu Thr Cys Leu Leu Asp Ile Leu Asp Thr Ala Gly Gln Glu Glu Tyr
50 55 60

Ser Ala Met Arg Asp Gln Tyr Met Arg Thr Gly Glu Gly Phe Leu Cys
65 70 75 80

Val Phe Ala Ile Asn Asn Thr Lys Ser Phe Glu Asp Ile His His Tyr
85 90 95

Arg Glu Gln Ile Lys Arg Val Lys Asp Ser Glu Asp Val Pro Met Val
100 105 110

Leu Val Gly Asn Lys Cys Asp Leu Pro Ser Arg Thr Val Asp Thr Lys
115 120 125

```
Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185


<210> SEQ ID NO 16
<211> LENGTH: 188
<212> TYPE: PRT
<213> ORGANISM: Homo sapiens

<400> SEQUENCE: 16

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185


<210> SEQ ID NO 17
<211> LENGTH: 9
<212> TYPE: PRT
<213> ORGANISM: Homo sapiens

<400> SEQUENCE: 17

Gly Ala Gly Gly Val Gly Lys Ser Ala
1               5


<210> SEQ ID NO 18
<211> LENGTH: 9
<212> TYPE: PRT
<213> ORGANISM: Homo sapiens

<400> SEQUENCE: 18

Gly Ala Asp Gly Val Gly Lys Ser Ala
1               5
```

<210> SEQ ID NO 19
<211> LENGTH: 24
<212> TYPE: PRT
<213> ORGANISM: Homo sapiens

<400> SEQUENCE: 19

```
Met Thr Glu Tyr Lys Leu Val Val Val Gly Ala Gly Gly Val Gly Lys
1               5                   10                  15

Ser Ala Leu Thr Ile Gln Leu Ile
            20
```

<210> SEQ ID NO 20
<211> LENGTH: 24
<212> TYPE: PRT
<213> ORGANISM: Homo sapiens

<400> SEQUENCE: 20

```
Met Thr Glu Tyr Lys Leu Val Val Val Gly Ala Asp Gly Val Gly Lys
1               5                   10                  15

Ser Ala Leu Thr Ile Gln Leu Ile
            20
```

<210> SEQ ID NO 21
<211> LENGTH: 26
<212> TYPE: DNA
<213> ORGANISM: Artificial Sequence
<220> FEATURE:
<223> OTHER INFORMATION: Synthetic

<400> SEQUENCE: 21

```
gccacagcac tgtgctcttg aagtcc                                          26
```

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22

```
caggcagtat ctggagtcat tgag                                            24
```

<210> SEQ ID NO 23
<211> LENGTH: 27
<212> TYPE: PRT
<213> ORGANISM: Artificial Sequence
<220> FEATURE:
<223> OTHER INFORMATION: Synthetic

<400> SEQUENCE: 23

```
Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25
```

<210> SEQ ID NO 24
<211> LENGTH: 137
<212> TYPE: PRT
<213> ORGANISM: Mus musculus

<400> SEQUENCE: 24

```
Asp Ile Gln Asn Pro Glu Pro Ala Val Tyr Gln Leu Lys Asp Pro Arg
1               5                   10                  15
```

-continued

```
Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 25
<211> LENGTH: 173
<212> TYPE: PRT
<213> ORGANISM: Mus musculus

<400> SEQUENCE: 25

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170


<210> SEQ ID NO 26
<211> LENGTH: 266
<212> TYPE: PRT
<213> ORGANISM: Artificial Sequence
<220> FEATURE:
<223> OTHER INFORMATION: Synthetic

<400> SEQUENCE: 26

Met Arg Gln Val Ala Arg Val Ile Val Phe Leu Thr Leu Ser Thr Leu
1               5                   10                  15

Ser Leu Ala Lys Thr Thr Gln Pro Ile Ser Met Asp Ser Tyr Glu Gly
```

```
            20                  25                  30

Gln Glu Val Asn Ile Thr Cys Ser His Asn Asn Ile Ala Thr Asn Asp
        35                  40                  45

Tyr Ile Thr Trp Tyr Gln Gln Phe Pro Ser Gln Gly Pro Arg Phe Ile
    50                  55                  60

Ile Gln Gly Tyr Lys Thr Lys Val Thr Asn Glu Val Ala Ser Leu Phe
65                  70                  75                  80

Ile Pro Ala Asp Arg Lys Ser Ser Thr Leu Ser Leu Pro Arg Val Ser
                85                  90                  95

Leu Ser Asp Thr Ala Val Tyr Tyr Cys Leu Val Gly Asp Met Asp Gln
            100                 105                 110

Ala Gly Thr Ala Leu Ile Phe Gly Lys Gly Thr Thr Leu Ser Val Ser
        115                 120                 125

Ser Asp Ile Gln Asn Pro Glu Pro Ala Val Tyr Gln Leu Lys Asp Pro
    130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Thr Val Leu Asp Met Lys Ala Met Asp Ser Lys Ser Asn Gly Ala Ile
            180                 185                 190

Ala Trp Ser Asn Gln Thr Ser Phe Thr Cys Gln Asp Ile Phe Lys Glu
        195                 200                 205

Thr Asn Ala Thr Tyr Pro Ser Ser Asp Val Pro Cys Asp Ala Thr Leu
    210                 215                 220

Thr Glu Lys Ser Phe Glu Thr Asp Met Asn Leu Asn Phe Gln Asn Leu
225                 230                 235                 240

Ser Val Met Gly Leu Arg Ile Leu Leu Leu Lys Val Ala Gly Phe Asn
                245                 250                 255

Leu Leu Met Thr Leu Arg Leu Trp Ser Ser
            260                 265


<210> SEQ ID NO 27
<211> LENGTH: 305
<212> TYPE: PRT
<213> ORGANISM: Artificial Sequence
<220> FEATURE:
<223> OTHER INFORMATION: Synthetic

<400> SEQUENCE: 27

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Gly Gln Thr Asn Tyr Gly Tyr Thr Phe Gly Ser Gly Thr Arg
```

```
        115                 120                 125

Leu Thr Val Val Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305


<210> SEQ ID NO 28
<211> LENGTH: 387
<212> TYPE: DNA
<213> ORGANISM: Artificial Sequence
<220> FEATURE:
<223> OTHER INFORMATION: Synthetic

<400> SEQUENCE: 28

atgaggcaag tggcgagagt gatcgtgttc ctgaccctga gtactttgag ccttgctaag      60

accacccagc ccatctccat ggactcatat gaaggacaag aagtgaacat aacctgtagc     120

cacaacaaca ttgctacaaa tgattatatc acgtggtacc aacagtttcc cagccaagga     180

ccacgattta ttattcaagg atacaagaca aaagttacaa acgaagtggc ctccctgttt     240

atccctgccg acagaaagtc cagcactctg agcctgcccc gggtttccct gagcgacact     300

gctgtgtact actgcctcgt gggtgacatg gaccaggcag gaactgctct gatctttggg     360

aagggaacca ccttatcagt gagttcc                                         387


<210> SEQ ID NO 29
<211> LENGTH: 396
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (385)..(385)
<223> OTHER INFORMATION: n is a, c, g, or t

<400> SEQUENCE: 29

atgggccccg ggctcctctg ctgggcactg ctttgtctcc tgggagcagg cttagtggac      60

gctggagtca cccaaagtcc cacacacctg atcaaaacga gaggacagca agtgactctg     120
```

-continued

```
agatgctctc ctaagtctgg gcatgacact gtgtcctggt accaacaggc cctgggtcag    180

gggccccagt ttatctttca gtattatgag gaggaagaga gacagagagg caacttccct    240

gatcgattct caggtcacca gttccctaac tatagctctg agctgaatgt gaacgccttg    300

ttgctggggg actcggccct ctatctctgt gccagcagct tgggacagac caactatggc    360

tacaccttcg gttcggggac caggntaacc gttgta                              396


<210> SEQ ID NO 30
<211> LENGTH: 10
<212> TYPE: PRT
<213> ORGANISM: Homo sapiens

<400> SEQUENCE: 30

Gly Ala Asp Gly Val Gly Lys Ser Ala Leu
1               5                   10


<210> SEQ ID NO 31
<211> LENGTH: 10
<212> TYPE: PRT
<213> ORGANISM: Homo sapiens

<400> SEQUENCE: 31

Val Gly Ala Asp Gly Val Gly Lys Ser Ala
1               5                   10


<210> SEQ ID NO 32
<211> LENGTH: 10
<212> TYPE: PRT
<213> ORGANISM: Homo sapiens

<400> SEQUENCE: 32

Val Gly Ala Gly Gly Val Gly Lys Ser Ala
1               5                   10


<210> SEQ ID NO 33
<211> LENGTH: 10
<212> TYPE: PRT
<213> ORGANISM: Homo sapiens

<400> SEQUENCE: 33

Gly Ala Gly Gly Val Gly Lys Ser Ala Leu
1               5                   10
```